United States Patent
Gattani et al.

(10) Patent No.: US 8,248,414 B2
(45) Date of Patent: Aug. 21, 2012

(54) MULTI-DIMENSIONAL NAVIGATION OF ENDOSCOPIC VIDEO

(75) Inventors: Abhishek Gattani, San Jose, CA (US); Salmaan Hameed, San Jose, CA (US)

(73) Assignee: Stryker Corporation, Kalamazoo, MI (US)

(*) Notice: Subject to any disclaimer, the term of this patent is extended or adjusted under 35 U.S.C. 154(b) by 805 days.

(21) Appl. No.: 11/523,217

(22) Filed: Sep. 18, 2006

(65) Prior Publication Data
US 2008/0071143 A1    Mar. 20, 2008

(51) Int. Cl.
*G06T 17/00*    (2006.01)
(52) U.S. Cl. ........................................................ 345/424
(58) Field of Classification Search ................. 600/117; 345/424
See application file for complete search history.

(56) References Cited

U.S. PATENT DOCUMENTS

| | | | |
|---|---|---|---|
| 5,109,276 A * | 4/1992 | Nudelman et al. ............ 348/47 |
| 5,383,454 A | 1/1995 | Bucholz |
| 5,417,210 A | 5/1995 | Funda et al. |
| 5,873,822 A * | 2/1999 | Ferre et al. .................. 600/407 |
| 5,912,720 A | 6/1999 | Berger et al. |
| 5,950,629 A | 9/1999 | Taylor et al. |
| 6,006,127 A | 12/1999 | Van Der Brug et al. |
| 6,038,467 A | 3/2000 | De Bliek et al. |
| 6,059,718 A * | 5/2000 | Taniguchi et al. ............ 600/117 |
| 6,135,946 A | 10/2000 | Konen et al. |
| 6,161,033 A | 12/2000 | Kuhn et al. |
| 6,167,296 A * | 12/2000 | Shahidi ......................... 600/427 |
| 6,229,547 B1 | 5/2001 | Grzeszczuk |
| 6,241,657 B1 * | 6/2001 | Chen et al. .................... 600/117 |
| 6,470,205 B2 | 10/2002 | Bosselmann et al. |
| 6,471,710 B1 | 10/2002 | Bucholtz |
| 6,546,277 B1 | 4/2003 | Franck et al. |
| 6,563,107 B2 | 5/2003 | Danisch et al. |
| 6,752,812 B1 | 6/2004 | Truwit |
| 6,782,284 B1 | 8/2004 | Subramanyan et al. |
| 6,832,985 B2 | 12/2004 | Irion et al. |
| 6,846,286 B2 | 1/2005 | Suzuki et al. |
| 7,423,640 B2 | 9/2008 | Guhring |
| 7,536,216 B2 * | 5/2009 | Geiger et al. ................. 600/407 |
| 7,646,945 B2 | 1/2010 | Jones et al. |
| 7,657,298 B2 | 2/2010 | Moctezuma de la Barrera et al. |

(Continued)

FOREIGN PATENT DOCUMENTS

WO    WO 2007/025081 A2    3/2007

OTHER PUBLICATIONS

Chao Zhang, et al., "Nonlinerar Distortion Correction in Endoscopic Video Images," Sep. 10, 2000, Proceedings of 2000 International Conference on Image Processing, pp. 439-442.

(Continued)

*Primary Examiner* — Edward Martello
(74) *Attorney, Agent, or Firm* — Blakely, Sokoloff, Taylor & Zafman LLP

(57) ABSTRACT

An endoscopic surgical navigation system comprises a multi-dimensional video generation module that enables a user to visually navigate captured endoscopic video with six degrees of freedom. This capability provides the user with control of a virtual camera (point of view) that can be translated in three orthogonal axes in 3-D space as well as allowing control of vertical panning (pitch), horizontal panning (yaw) and tilt (roll) of the virtual camera, as well as zoom.

17 Claims, 23 Drawing Sheets

U.S. PATENT DOCUMENTS

| | | | |
|---|---|---|---|
| 7,824,328 | B2 | 11/2010 | Gattani et al. |
| 7,945,310 | B2 | 5/2011 | Gattani et al. |
| 2002/0052546 | A1 | 5/2002 | Frantz et al. |
| 2002/0158870 | A1 | 10/2002 | Brunkhart et al. |
| 2003/0029464 | A1* | 2/2003 | Chen et al. ............ 128/922 |
| 2003/0038802 | A1 | 2/2003 | Johnson et al. |
| 2005/0085718 | A1 | 4/2005 | Shahidi |
| 2005/0182295 | A1* | 8/2005 | Soper et al. ........... 600/117 |
| 2005/0245810 | A1 | 11/2005 | Khamene et al. |
| 2006/0013523 | A1 | 1/2006 | Childers et al. |
| 2006/0235671 | A1* | 10/2006 | Kirchberg et al. ........ 703/11 |
| 2006/0267759 | A1 | 11/2006 | Levine |
| 2007/0013710 | A1 | 1/2007 | Higgins et al. |
| 2007/0061726 | A1* | 3/2007 | Rahn et al. ............. 715/719 |
| 2007/0276234 | A1 | 11/2007 | Shahidi |
| 2008/0071141 | A1 | 3/2008 | Gattani et al. |
| 2008/0071142 | A1 | 3/2008 | Gattani et al. |
| 2009/0063118 | A1* | 3/2009 | Dachille et al. ......... 703/11 |

OTHER PUBLICATIONS

Hill et al., "Fiber Bragg Grating Technology Fundamentals and Overview", Journal of Lighwave Technology, Aug. 1997, vol. 15, No. 8, p. 1268.

Lim et al., "Implicit Reconstruction of Solids from Cloud Point Sets," Proceedings of the Third ACM Symposium on Solid Modeling and Applications, May 17, 1995, pp. 393-402.

Office Action for U.S. Appl. No. 11/523,216, mailed May 27, 2009, 41 pages.

Office Action for U.S. Appl. No. 11/523,216, mailed Nov. 30, 2009, 37 pages.

Office Action for U.S. Appl. No. 11/523,216, mailed Jun. 3, 2010, 43 pages.

Office Action for U.S. Appl. No. 11/523,216, mailed Feb. 2, 2011, 44 pages.

Office Action for U.S. Appl. No. 11/523,136, mailed Apr. 24, 2009, 22 pages.

Office Action for U.S. Appl. No. 11/523,136, mailed Oct. 29, 2009, 18 pages.

Office Action for U.S. Appl. No. 11/523,391, mailed Mar. 30, 2009, 15 pages.

Office Action for U.S. Appl. No. 11/523,391, mailed Oct. 1, 2009, 12 pages.

Office Action for U.S. Appl. No. 11/523,391, mailed Mar. 26, 2010, 12 pages.

Office Action for U.S. Appl. No. 11/523,134, mailed Oct. 14, 2009, 16 pages.

Office Action for U.S. Appl. No. 11/523,136, mailed Nov. 30, 2010, 19 pages.

Office Action for U.S. Appl. No. 11/523,391, mailed Sep. 29, 2010, 10 pages.

Office Action for U.S. Appl. No. 11/523,136, mailed Apr. 13, 2011, 19 pages.

Office Action for U.S. Appl. No. 11/523,216, mailed Jun. 17, 2011, 50 pages.

Ellsmere, James, et al., "A Navigation System for Augmenting Laparoscopic Ultrasound", Downloaded Mar. 20, 2006, 8 pages.

Ellsmere, James, et al., "A new visualization technique for laparoscopic ultrasonography", *Sugery* Jul. 2004, Surgical Technique, 9 pages.

El-Sheik, Michael, MD., et al., Multiplanar Reconstructions and Three-dimensional Imaging (Computed Rotational Osteography) of Complex Fractures by Using a C-arm System: Initial Results, *Radiology* downloaded Aug. 30, 2006, http://radiology.rsnajnls.org/cgi/content/figsonly/221/3/843. 5 pages.

Hitachi Medical Systems America, "Multiplanar Reconstruction (MPR) Mode" downloaded Aug. 30, 2006, http://www.hitachimed.com/contentindex.asp?ID=700—1 page.

* cited by examiner

MULTI-DIMENSIONAL NAVIGATION OF ENDOSCOPIC VIDEO

FIELD OF THE INVENTION

At least one embodiment of the present invention pertains to medical devices, and more particularly, to a method and apparatus for enabling a user to navigate endoscope video with multiple degrees of freedom.

BACKGROUND

To reduce the trauma to patients caused by invasive surgery, minimally invasive surgical techniques have been developed for performing surgical procedures within the body through very small incisions. Endoscopy is a technique that is commonly employed in minimally invasive surgery. Endoscopy allows internal features of the body of a patient to be viewed through an endoscope, either directly or through video generated by a video camera coupled to the endoscope. The endoscope typically can also be used as a conduit through which other surgical instruments can be inserted into the body.

Endoscopes can be of the rigid type or the flexible type. A rigid endoscope is typically inserted into the body through a small external incision, as in laparoscopy, arthroscopy, etc. Flexible endoscopes, on the other hand, are commonly used in procedures where the endoscope is inserted through a natural body orifice, such as the mouth or anus, as in gastroscopy or colonoscopy, respectively.

Endoluminal surgery is a newer form of minimally-invasive surgery, in which the surgical instrument (i.e., the endoscope or an instrument inserted through it) initially enters the body through a natural bodily orifice, such as the mouth. Typically a flexible endoscope is used. The instrument is then "threaded" through a natural body lumen, such as the esophagus, until its distal tip is close to the target anatomy. Often the target anatomy is not in the immediate proximity of the orifice of entry, however. Therefore, the surgeon must navigate the endoscope to the target anatomy and may have to operate on portions of the anatomy that are not directly visible or are not easily visible.

Because endoscopes have limited field of view, localization of target lesions and navigation to the desired areas through small entry points can be difficult. Furthermore, some parts of the body contain extremely small and/or complex structures that are difficult for a surgeon to see through an endoscope or in endoscopic video. The challenges become larger as the distance from the entry point to the target anatomy increases, as is the case in endoluminal surgery.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

Figure 1:
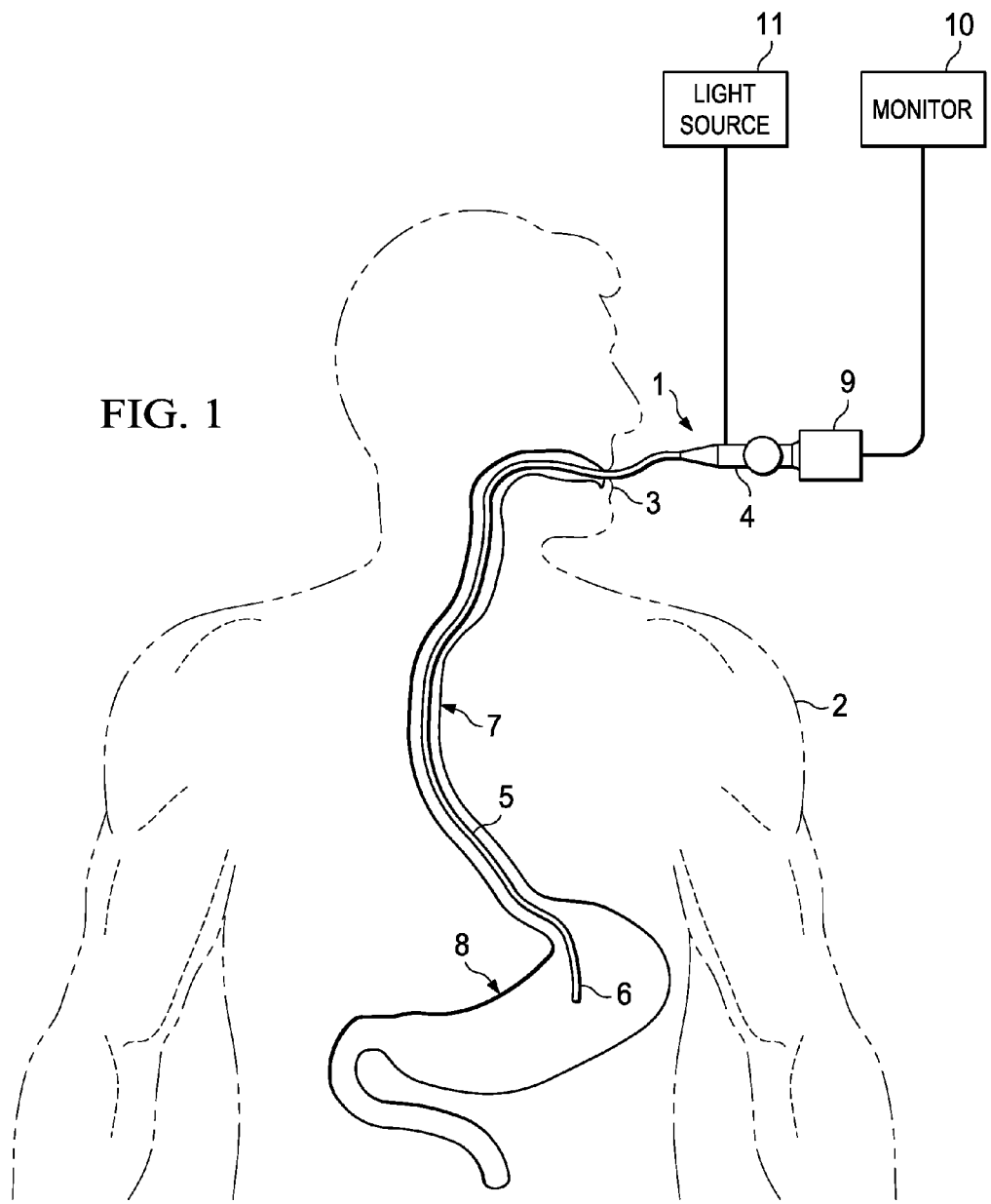
FIG. 1 is a high level diagram of a system for performing endoluminal surgery.

A visual navigation system for use in endoscopic surgery, particularly (though not exclusively) in endoluminal surgery, is described. References in this specification to "an embodiment", "one embodiment", or the like, mean that the particular feature, structure or characteristic being described is included in at least one embodiment of the present invention. Occurrences of such phrases in this specification do not necessarily all refer to the same embodiment.

In view of the challenges mentioned above, it is desirable to provide a visual navigation system to provide coupled three-dimensional (3D) visualization and navigation assistance to the surgeon in navigating an endoscope to the target anatomy, particularly during endoluminal surgery. As described in greater detail below, therefore, according to certain embodiments of the invention, a visual navigation system (VNS 30) comprises a data acquisition subsystem, an endoscope tracking subsystem, a registration subsystem, a data processing subsystem and a user interface subsystem. The data acquisition subsystem inputs intra-operative scan data from a medical scanning device during an endoscopic procedure. The tracking subsystem captures data representing positions and orientations of a flexible endoscope during the endoscopic procedure. The registration subsystem determines transformation parameters for coregistering the intra-operative scan data and the data indicative of positions and orientations of the endoscope. The data processing subsystem coregisters the intra-operative scan data and the data indicative of positions and orientations of the endoscope based on the transformation parameters and generates real-time image data representing 3D internal views of a body that are coregistered with live video from an endoscopic video camera. The user interface subsystem receives input from a user for controlling the system and provides output to the user.

The following definitions and explanations shall apply to terms used herein:

"Coregistering" means bringing into a common coordinate space and orientation.

"Flexible" means designed to be flexed substantially without incurring damage to the instrument (not just capable of being deformed).

A "flexible endoscope" is an endoscope, a substantial portion of the length of which is flexible, including the distal end. (A "flexible endoscope" can and usually does have a rigid proximal portion, or "base".)

"Intra-operative scan data" is scan data acquired by a scan performed during a particular endoscopic procedure on a body. This term does not include video acquired from an endoscopic video camera.

"Logic" can be or include (but is not limited to) any one or more of: special-purpose hardwired circuitry, programmable circuitry, software, firmware, or any combination thereof.

A "module" means any one or more of: special-purpose hardwired circuitry; software and/or firmware in combination with one or more programmable processors; or any combination thereof.

"Positions" is synonymous with "locations".

"Pre-operative scan data" is scan data acquired by a scan performed prior to a particular endoscopic procedure on a body.

During an endoscopic procedure on a body, the VNS inputs intra-operative scan data generated by a medical scanning device, such as an x-ray computed tomography (CT) device, an MRI device, ultrasound imaging device, etc. The intra-operative scan data is representative of a region of interest in the body. The VNS also captures data indicative of positions and orientations of a flexible endoscope during the endoscopic procedure, from various sensors on the endoscope. The VNS further generates real-time three-dimensional scan images of the region of interest based on the intra-operative scan data and/or the pre-operative scan data and the data indicative of positions and orientations of the flexible endoscope. The VNS coregisters the real-time three-dimensional scan images with live video images generated by the endoscopic video camera that is coupled to the endoscope. The VNS then causes the real-time three-dimensional (volumetric) scan images and the live video images to be displayed coregistered on a display device.

The VNS can automatically detect movement of the flexible endoscope during an endoscopic procedure and, in response, identify a particular slice of scan data corresponding to a current location and orientation of the endoscope tip and cause an image of the slice to be displayed, and similarly cause other slices of scan data to be displayed in response to additional movements of the endoscope.

The VNS can also coregister and display the intra-operative scan data with pre-operative scan data representative of the region of interest in the body and generated prior to the endoscopic procedure by a medical scanning device.

Another feature of the VNS is the ability to correct for barrel lens distortion in the live video. Barrel lens distortion is divergence, in the acquired endoscopic video, from the rectilinear projection in geometric optics where image magnification decreases with increasing distance from the optical axis.

Another feature of the VNS is a technique for employing model-fitting technique which enables a user easily to obtain in vivo measurements of anatomical features in the body during an endoscopic procedure.

Yet another feature of the VNS is that it enables a user to visually navigate captured endoscopic video with six degrees of freedom. This capability provides the user with control of a virtual camera (point of view) that can be translated in three orthogonal axes in 3-D space as well as allowing control of vertical panning (pitch), horizontal panning (yaw) and tilt (roll) of the virtual camera, as well as zoom.

Still another feature of the VNS is surgical instrument path correlation. In particular, the VNS can compute the path taken by an endoscope scope (or other medical instrument) during a procedure and various related attributes and parameters, and can compute and display a correlation between two paths.

I. Overall System Architecture and Operation

FIG. 1 is a high level diagram of a system for performing endoluminal surgery. A flexible endoscope ("scope") 1 is inserted into the body of a patient 2 through a natural orifice, such as the mouth 3. The scope 1 includes a rigid base 4 and a flexible portion 5 which is inserted into the body. The distal tip 6 of the scope 1 is part of the flexible portion 5 and can be flexed about two or more orthogonal axes by the surgeon, by using controls (not shown) mounted on the base 4. The surgeon navigates the scope 1 through a natural body lumen, such as the esophagus 7 and stomach 8 until the distal tip 6 of the scope 1 is in proximity to the target anatomy.

Optically coupled to the base 4 of the scope 1 is an endoscopic video camera 9, which outputs a video signal to a display device (monitor) 10, which may be, for example, a cathode ray tube (CRT) display, liquid crystal display (LCD), or other suitable type of display device. High-intensity light from a light source 11 is provided through a light conduit to a light port on the base 4 of the scope 1 and is transmitted through the flexible portion 5 and output through the distal tip 6. The scope 1 may include an instrument channel (not shown), through which a surgical instrument (such as a grabbing instrument for biopsies) can be passed through to an opening at the distal tip 6. The entry port for the instrument channel is normally on or near the base 4 of the scope 1.

Figure 2:
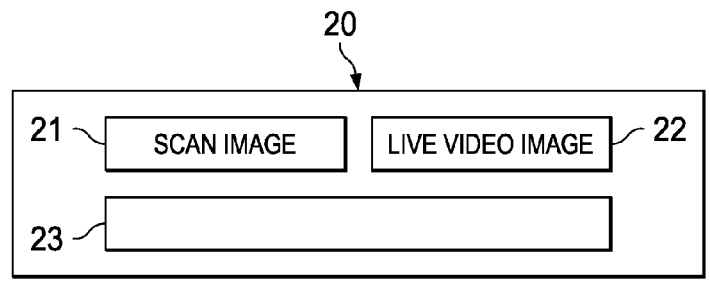
FIG. 2 schematically illustrates an example of a display of multiple coregistered, multi-modal images.

As noted above, the VNS introduced here (not shown in FIG. 1) provides a display that includes coregistered views of intra-operative scan images and/or intra-operative scan images with live endoscopic video, among other features. FIG. 2 illustrates schematically how such a display may be presented to a user. The VNS may include its own display device, on which such a display can be presented. Alternatively, the display can be presented on a separate external display device that is connected to the VNS 30, such as the monitor 10.

As shown in FIG. 2, a display 20 generated by the VNS includes several windows in proximity to each other, including a window 21 that contains a scan image and a window 22 that contains a corresponding live video image, presented side-by-side. The scan image is generated and updated in real-time based on intra-operative scan data acquired during the endoscopic procedure from a CT scanning device, MRI device, ultrasonic imaging device, or other medical scanning device. The scan image is coregistered with the live video image, according to the technique described herein. Other data, such as text, graphics, touchscreen controls, etc., can be included on a separate portion 23 of the display 20.

Figure 3:
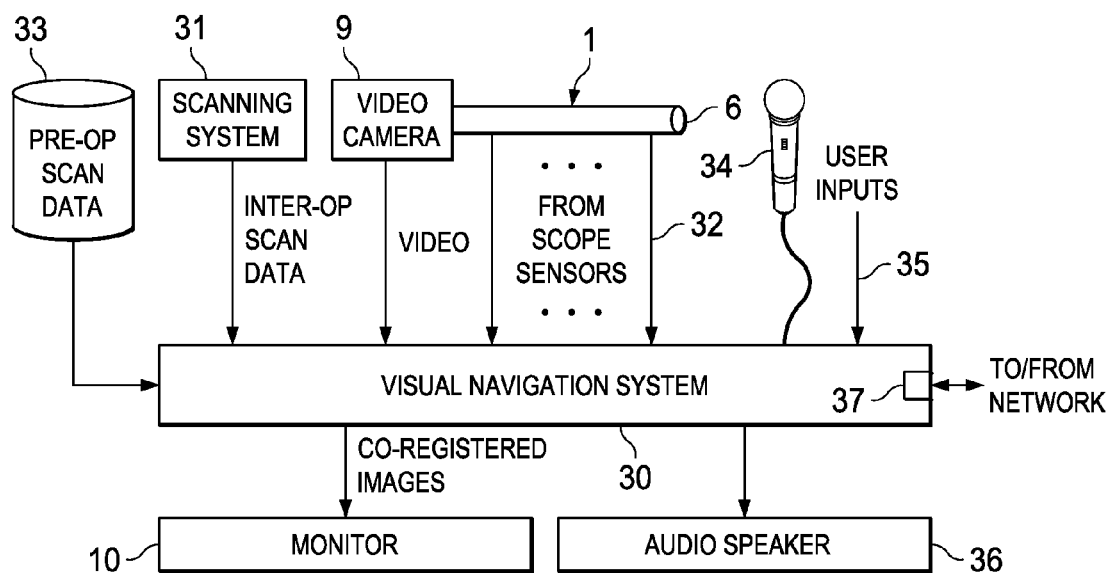
FIG. 3 schematically illustrates an endoscopic surgery visualization system that includes a Visual Navigation System (VNS)

FIG. 3 schematically illustrates an endoscopic surgery visualization system that includes the VNS 30. The VNS 30 receives intra-operative scan data from a medical scanning system 31, which can be, for example, a CT system, MRI system, ultrasonic imaging system, or the like. The VNS 30 also receives live video from the endoscopic video camera 9 that is coupled to the scope 1. The VNS 30 also receives inputs 32 from various sensors on the endoscope 1, which are used to determine the current position and orientation of the distal tip 6 of the endoscope 1. The VNS 30 may also input pre-operative scan data from a data storage facility 33 (e.g., a computer hard drive, file server, or the like). The pre-operative scan data can be coregistered with the intra-operative scan data and or the live video.

The VNS 30 may have speech recognition/voice response capability; in that case, the VNS 30 further receives audio inputs from a microphone 34, through which to receive voice commands. The VNS 30 may also receive various other user inputs 35, such as from touchscreen controls or other input devices such as a keyboard, mouse, buttons, switches, etc. The VNS 30 outputs coregistered images such as described above to its own display device, if it is so equipped, and/or to an external monitor 10. The VNS 30 may also output synthesized speech and/or other forms of audible output (e.g., warnings or distance to target) to the user through an audio speaker 36. The VNS 30 may also include a network interface 37 through which to transmit and/or receive data over a network, such as a local-area network (LAN), a wide area network (WAN), a corporate intranet, the Internet, are any combination thereof. The VNS 30 may also include a separate video camera and appropriate software (not shown) to capture and recognize gestures of the user as commands, in real-time, and to cause corresponding actions to be performed.

Figure 4:
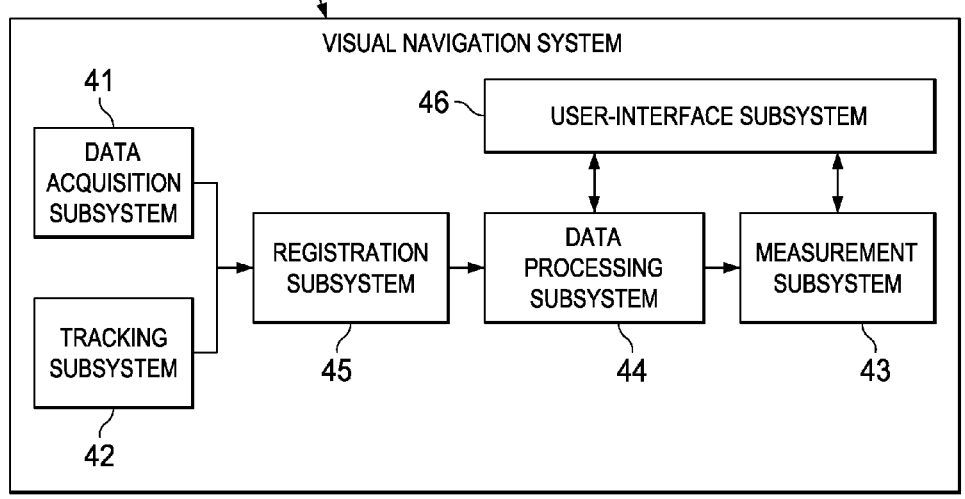
FIG. 4 is a block diagram showing the elements of the VNS, according to certain embodiments of the invention.

FIG. 4 is a block diagram showing the major subsystems of the VNS 30, according to certain embodiments of the invention. As shown, the VNS 30 includes a data acquisition subsystem 41, a scope tracking subsystem 42, a measurement subsystem 43, a data processing subsystem 44, a registration subsystem 45 and a user interface subsystem 46. The purpose of the data acquisition subsystem 44 is to load intra-operative and pre-operative scan data representative of a region of interest of a given patient. The purpose of the registration subsystem is to bring the various data acquired into a common coordinate space. The registration subsystem 45 determines the transformation parameters needed to coregister the data acquired by the data acquisition subsystem 41 and the tracking subsystem 42 to a common coordinate space. These parameters are passed to the data processing subsystem 44, which transforms the input data, performs segmentation and creates the desired visualizations. The data processing subsystem is the main processing subsystem of the VNS 30.

The visualizations are passed to the user interface subsystem 46 for audio and visual output. The user interface subsystem 46 also interprets and passes user commands received in the form of any one or more of: voice, gestures, touch screen inputs, button presses, etc.

The purpose of the endoscope tracking subsystem 42 is to capture, in real-time, data indicative of the position and orientation of the endoscope, particularly its distal tip, to enable coregistration of multi-modal images. Note, however, that the techniques introduced here can also be used to track a surgical instrument other than an endoscope, such as a catheter, guide wire, pointer probe, stent, seed, or implant.

The measurement subsystem 43 receives user inputs and processed data via the data processing subsystem 44, computes measurements of anatomical features, and formats the results to be passed to the user interface subsystem 46 for audio and/or visual output. These subsystems are described further below.

Figure 5:
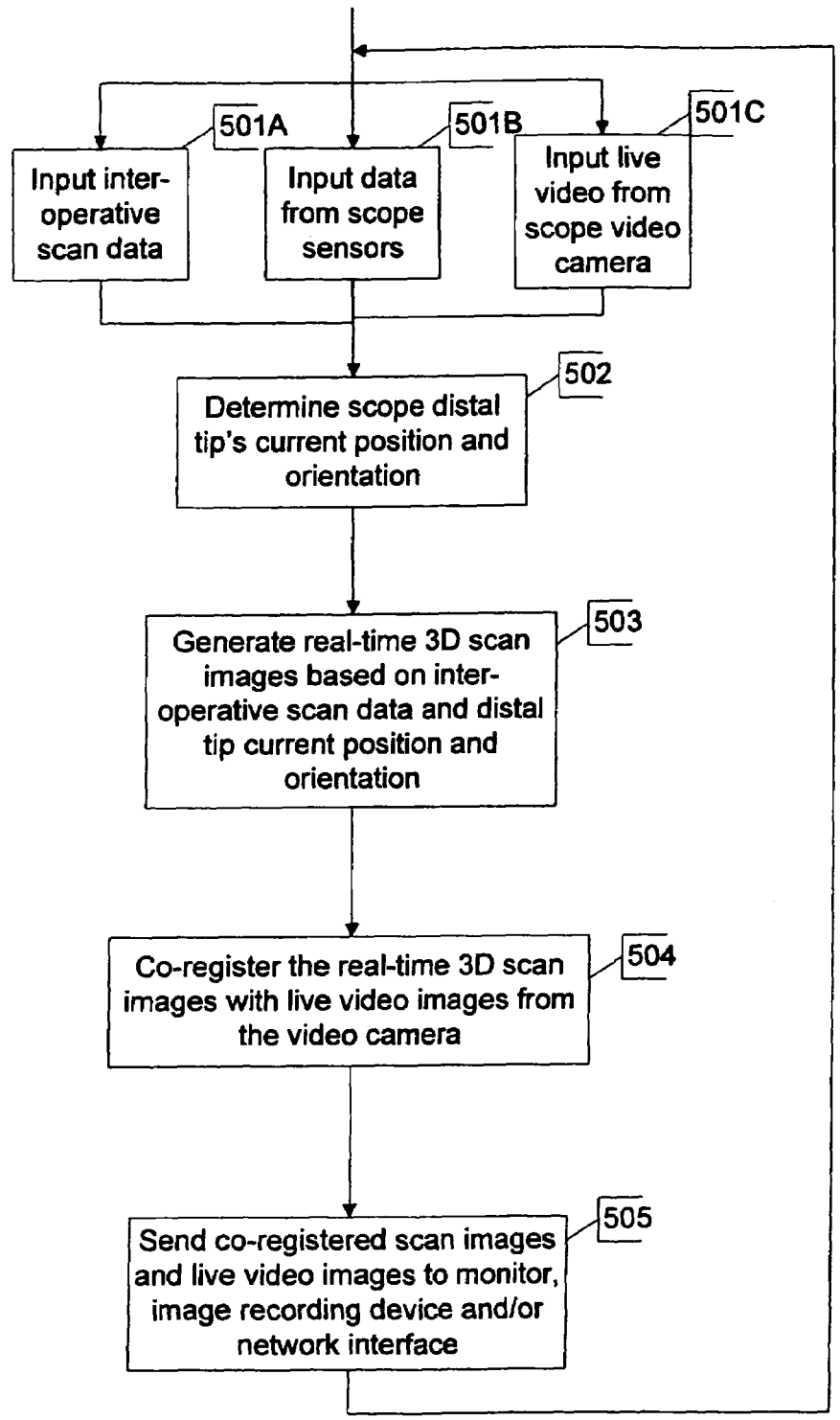
FIG. 5 illustrates an example of the overall process that can be performed by the VNS while the VNS is in a particular operating mode to coregister multi-modal images.

FIG. 5 illustrates an example of a process that can be performed by the VNS 30, according to certain embodiments of the invention, while the VNS 30 is in an operating mode to coregister scan images and live video images. Initially, the VNS 30 concurrently inputs intra-operative scan data, position/orientation data from the sensors on the scope, and live video from the endoscopic video camera, at 501a, 501b and 501c, respectively. At 502 the VNS 30 determines the current position and orientation of the scope's distal tip. At 503 the VNS 30 generates real-time 3-D (volumetric) scan images, based on the intra-operative scan data and the current position and orientation of the scope's distal tip. The VNS 30 then coregisters the real-time 3-D scan images with the live video from the endoscopic video camera at 504. The coregistered scan images and live video are then sent to a monitor (which may be integral with or external to the VNS 30) for display, to an image recording device for recording, and/or to a network interface for transmission over a network. The process then repeats from the beginning with new data while the VNS 30 is in this operating mode. It should be understood that the process of FIG. 5 is illustrated and described here at a conceptual level; consequently, the exact sequence of operations shown in FIG. 5 does not necessarily have to be the actual sequence in practice. For example, input data can be received (501a, 501b and 501c) and buffered as necessary while the other operations in the process are being performed on previously received data (i.e., pipelined processing).

Figure 6:
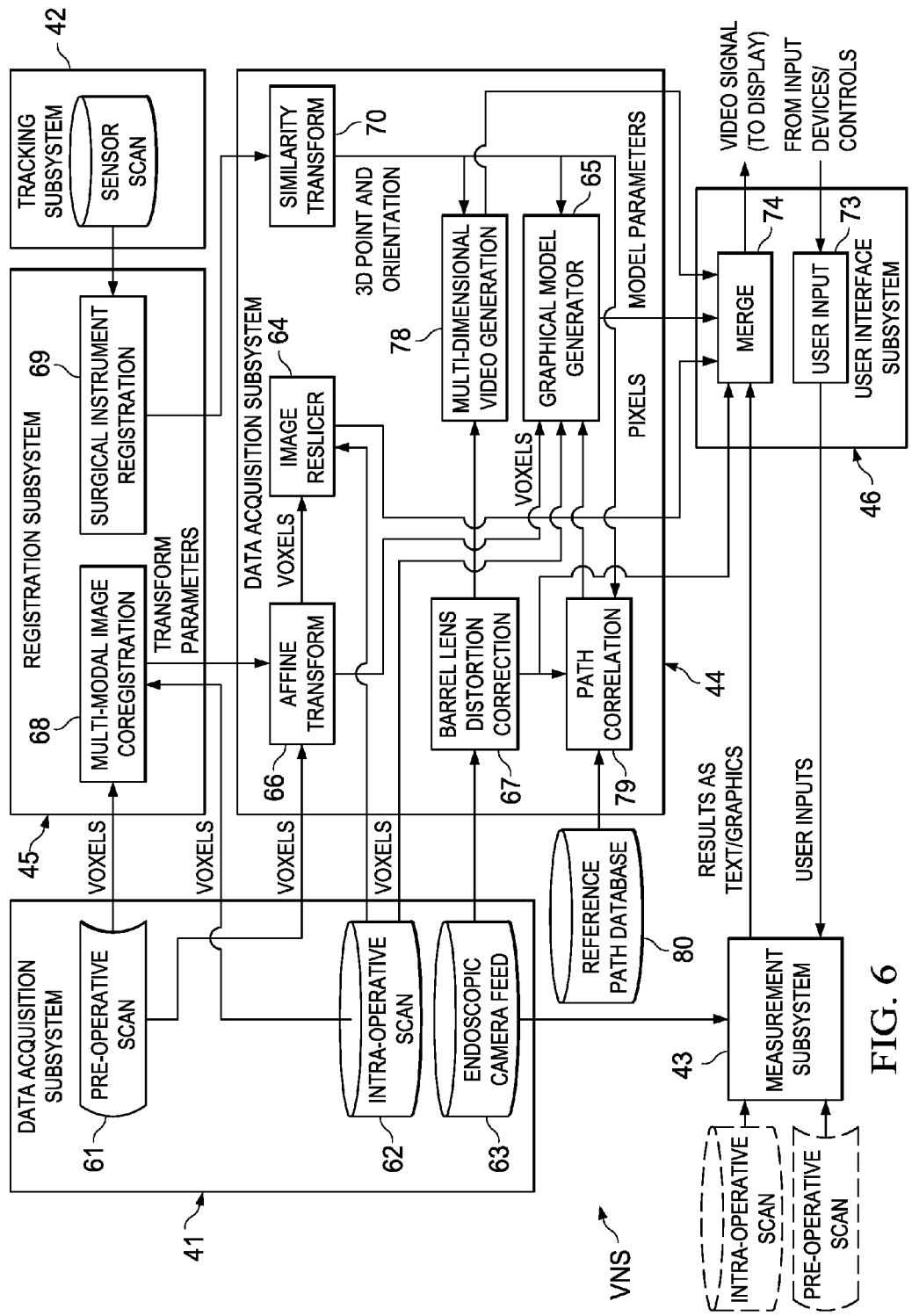
FIG. 6 is a block diagram showing the VNS in greater detail, according to certain embodiments of the invention.

FIG. 6 shows the architecture of the VNS 30 in greater detail. The subsystems of the VNS 30 shown in FIG. 4 will now be further described with reference to FIG. 6.

The purpose of the data acquisition subsystem 44 is to load scan data representative of a region of interest of a given patient. This subsystem includes the following three modules:

1) An interface 62 to an intra-operative imaging device (e.g., CT device, MRI device, positron emission tomography (PET) device, fluoroscopy device, ultrasound device) to receive real-time intra-operative scan data from such device and to configure and read the scan data. This can be, for example, software within the imaging device.
2) An image reader module 61 to read medical images stored in, for example, DICOM format, for loading pre-operative scan data. The pre-operative scan data can be from, for example, an MRI scan, CT scan, PET scan, fluoroscopic scan, or ultrasound scan.

3) A video interface 63 to the endoscopic video camera feed, to receive and capture real-time intra-operative video of the patient's anatomy. This interface can be, for example, a Firewire interface, Universal Serial Bus (USB) interface, RS-232 interface, or the like, along with a frame grabber and appropriate software to package frames as a real-time feed.

The purpose of the endoscope tracking subsystem 42 is to capture, in real-time, data indicative of the position and orientation of the endoscope, particularly its distal tip. Note, however, that the techniques introduced here can also be used to track a surgical instrument other than an endoscope, such as a catheter, guide wire, pointer probe, stent, seed, or implant.

The data processing subsystem 44 is the main processing subsystem of the VNS 30. In the illustrated embodiment, this subsystem includes an image reslicer 64, a graphical model generator 65, an affine transform module 66, a rigid (similarity) transform module 70, a barrel-distortion correction module 67, a multi-dimensional video generation module 78, and a path correlation module 79.

The image reslicer 64 produces reformatted images from scan data to desired positions and orientations. A reformatted image is derived by arbitrarily orienting a plane in 3D space, and assigning values to each 2D pixel of the slice by interpolating the 3D voxels of the volume data intersected by the plane.

The graphical model generator 65 generates surface models of the anatomical region of interest from the patient scan data provided by the data acquisition subsystem 41. This module provides two types of images:

1) A volumetric perspective image which is rendered from a point of view that correlates to one of the position/orientation sensors attached to the endoscope.
2) A volumetric perspective image which is rendered from a point of view that correlates to the position and orientation of the patient. This will allow the surgeon to have, in effect, "x-ray vision", to see the neighboring anatomy relative to the position of the surgical instrument.

The graphical model generator 65 provides segmentation functions such as thresholding, automatic detection of borders, creation of objects within the volume, extraction of surfaces, and further provides visualization functions, e.g., rendering using different parameters (depth shading, gradient shading, maximum intensity projection, summed voxel projection, surface projection, transparency shading).

Figure 9:
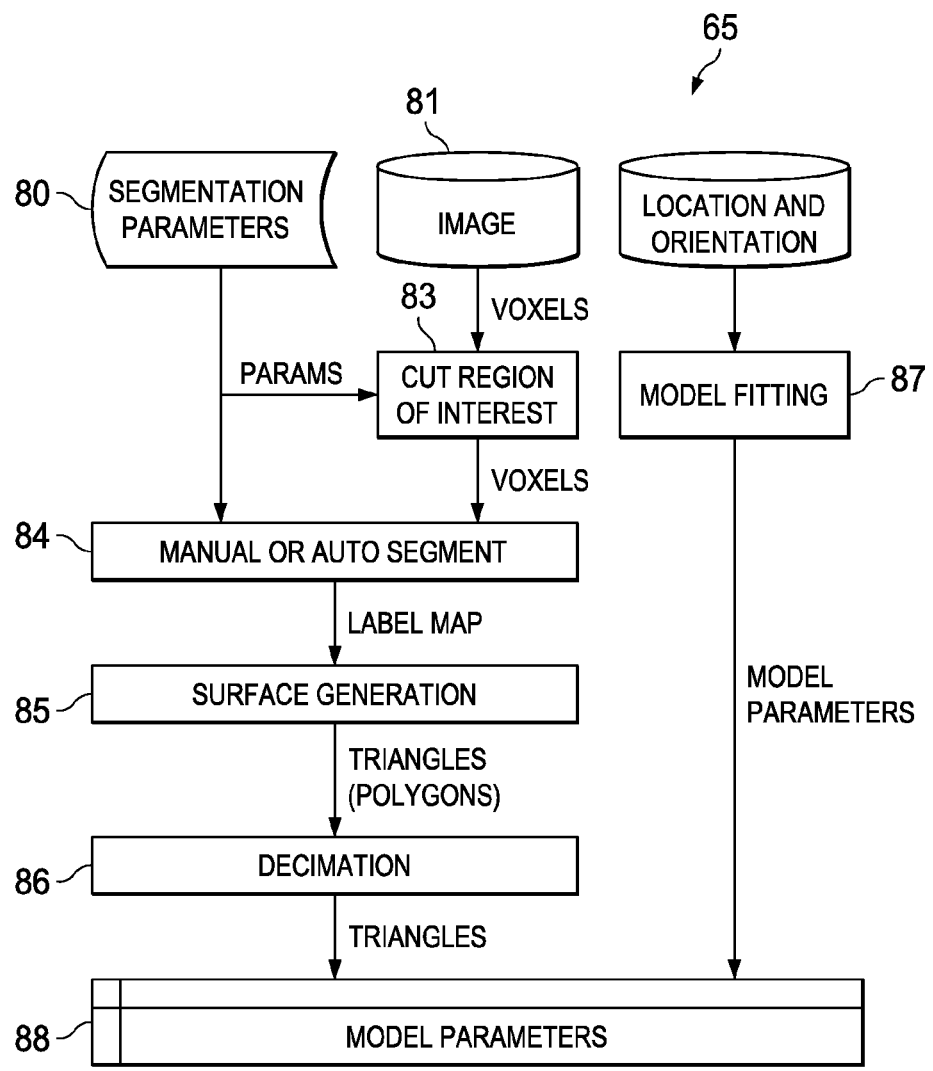
FIG. 9 is a block diagram showing the model generator according to certain embodiments of the invention.

FIG. 9 is a block diagram showing the graphical model generator 65 according to certain embodiments of the invention. The segmentation parameters, such as threshold, histogram, region of interest, shape a prioris, etc., are loaded from a file for that anatomical region. The input image volume 81 is cropped (cut) to the specified region of interest (ROI) by a Cut ROI unit 83. The segmentation unit 84 then applies a segmentation algorithm on the cropped volume. An example of the segmentation algorithm is the well-known seeded region growing. Other segmentation algorithms, such as level sets, can also be used. The output of the segmentation unit 84 is a label map that specifies which pixels belong to the segmented object and which do not. The label map is sent as input to the surface generation unit 85, which in one embodiment applies the marching cubes algorithm, i.e., by using polygons (e.g., triangles) to represent the segmented surface. Since the number of triangles can be very large, the decimation unit 86 applies a decimation algorithm to reduce the triangles and produce a smoother surface. The triangles are reduced so that more can fit into the graphics card memory (not shown).

In parallel with the above-described operations, the data representative of the co-registered location and orientation of the tracked scope is passed as input to the model fitting unit 87. The model fitting unit 87 fits a predetermined model to the data received. In one embodiment the model used to represent the tracked surgical instrument is a line. The model fitting unit 87 produces model parameters 88, such that the position and orientation of the line (i.e., the model) is the same as that of the scanned data. The model parameters 88 are then sent to the merge module 74 for rendering.

Referring again to FIG. 6, the transform modules 66 and 70 apply a geometric transform to 3D points. The inputs expected by the transform modules 66 and 70 are an image, a transform and the output of an interpolation function. The interpolation is required since the mapping from one space to another will often require evaluation of the intensity of the image at non-grid positions. Nearest neighbor interpolation is an example of the type of interpolation that can be used in this regard.

The transform modules 66 and 70 include affine transform module 66 and similarity transform module 70. A similarity (or "rigid") transform is defined as a transformation that preserve magnitudes of all lengths and angles. An affine transform is defined as a transformation which preserves parallelism of lines and includes rotation, scaling, shearing and translation. Each of the transforms is specified by an N×N matrix and an N×1 vector, where N is the space dimension. The number of parameters is (N+1)×N. The first N×N parameters define the matrix in column-major order (where the column index varies the fastest). The last N parameters define the translation for each dimension. The number of dimensions is three (3).

The barrel distortion correction module 67 corrects the barrel distortion inherent in endoscopic video in order to facilitate accurate measurements and one-to-one comparison with visualization. Barrel distortion is a divergence from the rectilinear projection in geometric optics where image magnification decreases with increasing distance from the optical axis. This type of distortion is a lens aberration or defect that causes straight lines to bow outward, away from the center of the image. The inverse mapping function used to correct the barrel lens distortion can be determined a priori, or it can be obtained from the manufacturer of the endoscopic video camera.

The multi-dimensional video generation module 78 processes video frames acquired by the endoscopic video camera, to enable a user to navigate the captured video with six degrees of freedom. This feature is described in detail below.

The path correlation module 79 computes the path taken by the scope (or other medical instrument) during a procedure and various related attributes and parameters, and can compute and display a correlation between two paths. This feature is also described in detail below.

The purpose of the registration subsystem 45 is to bring the various data acquired into a common coordinate space. This subsystem includes a multi-modal image coregistration module 68 and a surgical instrument registration module 69.

Figure 7:
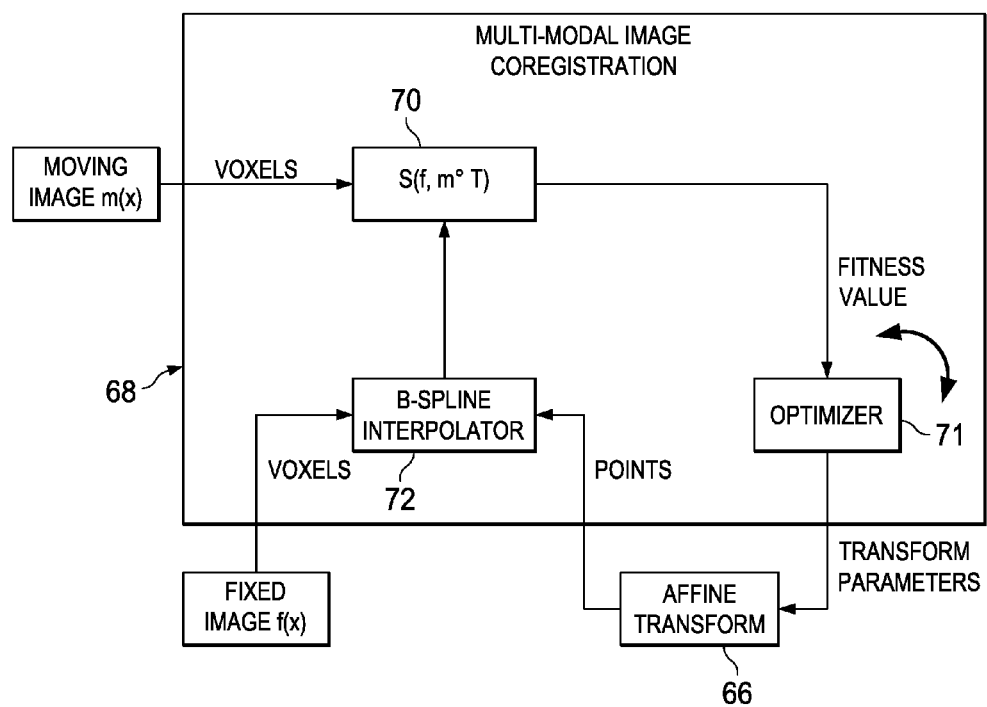
FIG. 7 is a block diagram showing an example of the implementation of the multi-modal image coregistration module.

The multi-modal image coregistration module 68 coregisters pre-operative patient scan data with intra-operative patient scan data. Image coregistration is the process of determining the spatial transform that maps points from one image to the homologous points on a second image. FIG. 7 is a block diagram showing an example of an implementation of the multi-modal image coregistration module 68. Input data to the coregistration process includes two images: one is defined as the "fixed image" f(X), which may be, for example, an MRI image; the other is defined as the "moving image" m(X), which may be, for example, a CT image. The output of the multi-modal image coregistration module is parameters of an affine transformation matrix. The fixed image f(X) is the intra-operative patient scan data and the moving image m(X) is the pre-operative patient scan data. The transform module T(X) represents the spatial mapping of points from the fixed image space to points in the moving image space. The metric module 70 performs a function S(f, m∘T) to provide a measure of how well the fixed image is matched by the transformed moving image and outputs this as a fitness value to the optimizer 71. The optimizer 71 continues invoking the affine transform module 66 with different parameters until an optimal value for the metric has been reached or a maximum allowed number of iterations is complete. In one embodiment, the well-known Mutual Information based Image-to-Image Metric is used for the metric module; affine transformation is used for the transformation module; and gradient descent optimization is used for the optimizer. Low-pass filtering of the images can be used to increase robustness against noise. In such cases the low-pass filter can be a Gaussian image filter.

When an affine transformation is applied, many pixels in the output image do not have a corresponding input. That is, the corresponding input falls in the middle of other voxels. The B-spline interpolator 72 is therefore used to interpolate the voxel value at the output.

Referring again to FIG. 6, the surgical instrument registration module 69 brings the data acquired by the tracking subsystem 42 into a common co-ordinate space. This module takes data indicative of the position and orientation of the endoscope when placed on the origin of the co-ordinate system of the intra-operative imaging device as the parameters of the rigid transformation matrix.

The user interface subsystem 46 takes user input from, and provides audio and visual output to, the user (e.g., the surgeon). This subsystem includes a user input module 73 and a merge module 74. The merge module 74 mixes graphical models from the graphical model generator 65, image slices from the image reslicer 64, endoscopic video from endoscopic video camera (via the barrel lens distortion correction module 67), and text at the desired position, orientation, resolution, and opacity, and produces an image. The displays generated by the merge module 74 include the following types of windows, any two or more of which can be displayed simultaneously and coregistered with each other:

1) Three orthogonal slices of the volume based on scan data: transversal slice, sagittal slice, and coronal slice.
2) A rendering window that includes a volumetric perspective image, based on scan data, rendered from a point of view that correlates to the outputs of the position/orientation sensors attached to the endoscope (i.e., the endoscopic camera point of view).
3) A rendering window that includes a volumetric perspective image, based on scan data, rendered from a point of view that correlates to the position and orientation of the patient (not necessarily the camera point of view; e.g., from the surgeon's eye point of view).
4) A video image from the endoscopic video camera (after barrel-distortion correction).

Figure 8:
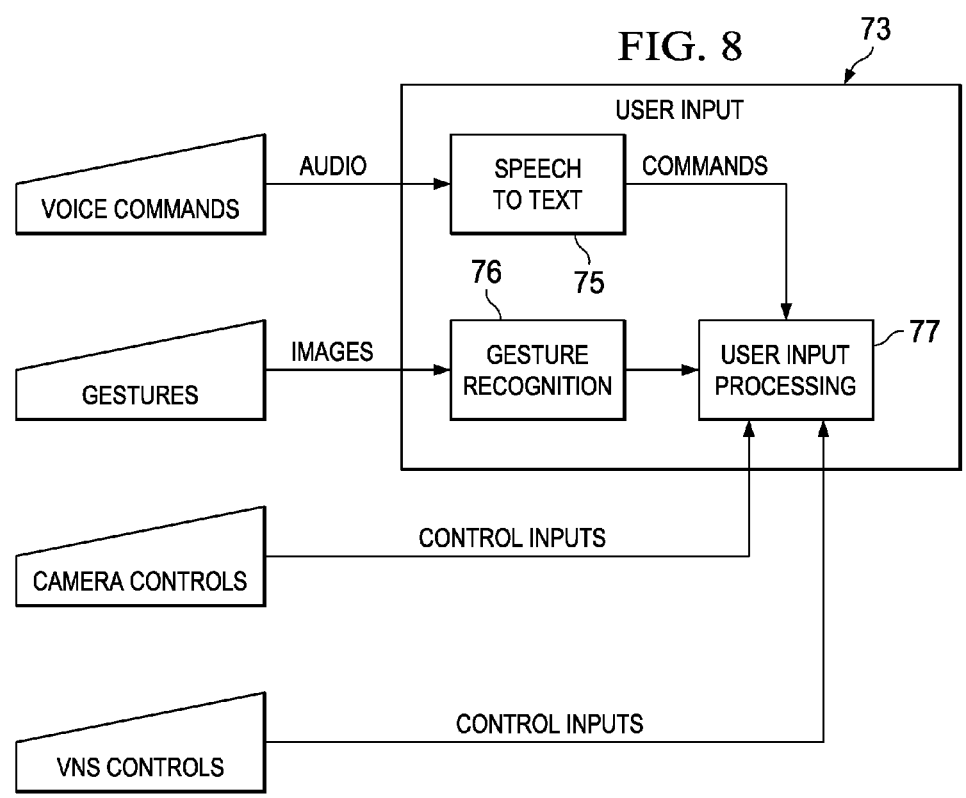
FIG. 8 is a block diagram showing an example of the user input portion of the user interface subsystem.

FIG. 8 is a block diagram showing the user input module 73 of the user interface subsystem 46. The user input module 73 includes a speech-to-text converter 75, a gesture recognition module 76, and an input module 77 to receive the outputs of those modules and to receive user inputs from camera controls on the endoscopic video camera and from controls on the VNS 30.

In operation, data generated by the intra-operative scanning device is coregistered with the pre-operative scan at the beginning of the endoscopy procedure. The output of the coregistration is affine transform parameters. This transformation is applied to the pre-operative scan data on iterations of intra-operative data acquisitions. The coregistered patient scan is processed for visualization, i.e., model generation of anatomical regions of interest. The model is sent to the merge module 74 for mixing with other models, images and text. The position/orientation data from the sensors on the scope is also registered to the common co-ordinate space and sent to the model generator to provide a simulation of the surgical instrument, to be mixed by the merge module 74.

Data from the intra-operative scan is also processed for visualization, i.e., model generation of anatomical regions of interest. The model is sent to the merge module 74 for mixing with other models, images and text. The image reslicer module 64 generates slices of the pre-operative or intra-operative scan. The selection of the current slices (transversal, coronal, sagittal) is done either by user-input or automatically by the tracking subsystem using a defined position on the endoscope, e.g., the distal tip, as reference. The video from the endoscopic camera feed is corrected for barrel lens distortion and then sent to the merge module 74 for mixing with other models, images and text.

As noted above, the tracking subsystem 42 can automatically detect movements of the flexible endoscope during an endoscopic procedure. Specific techniques and apparatus for detecting the current position and orientation of the scope are described below. In response to scope movements, the data processing subsystem 44 can also automatically identify a particular slice of intra-operative or pre-operative scan data corresponding to the current location and orientation of the endoscope tip and cause an image of that slice to be displayed to the user from the viewpoint of the scope tip or another viewpoint, and in the same way cause other slices of intra-operative or pre-operative scan data to be identified and displayed automatically in response to further movements of the endoscope during the procedure.

Figure 22:
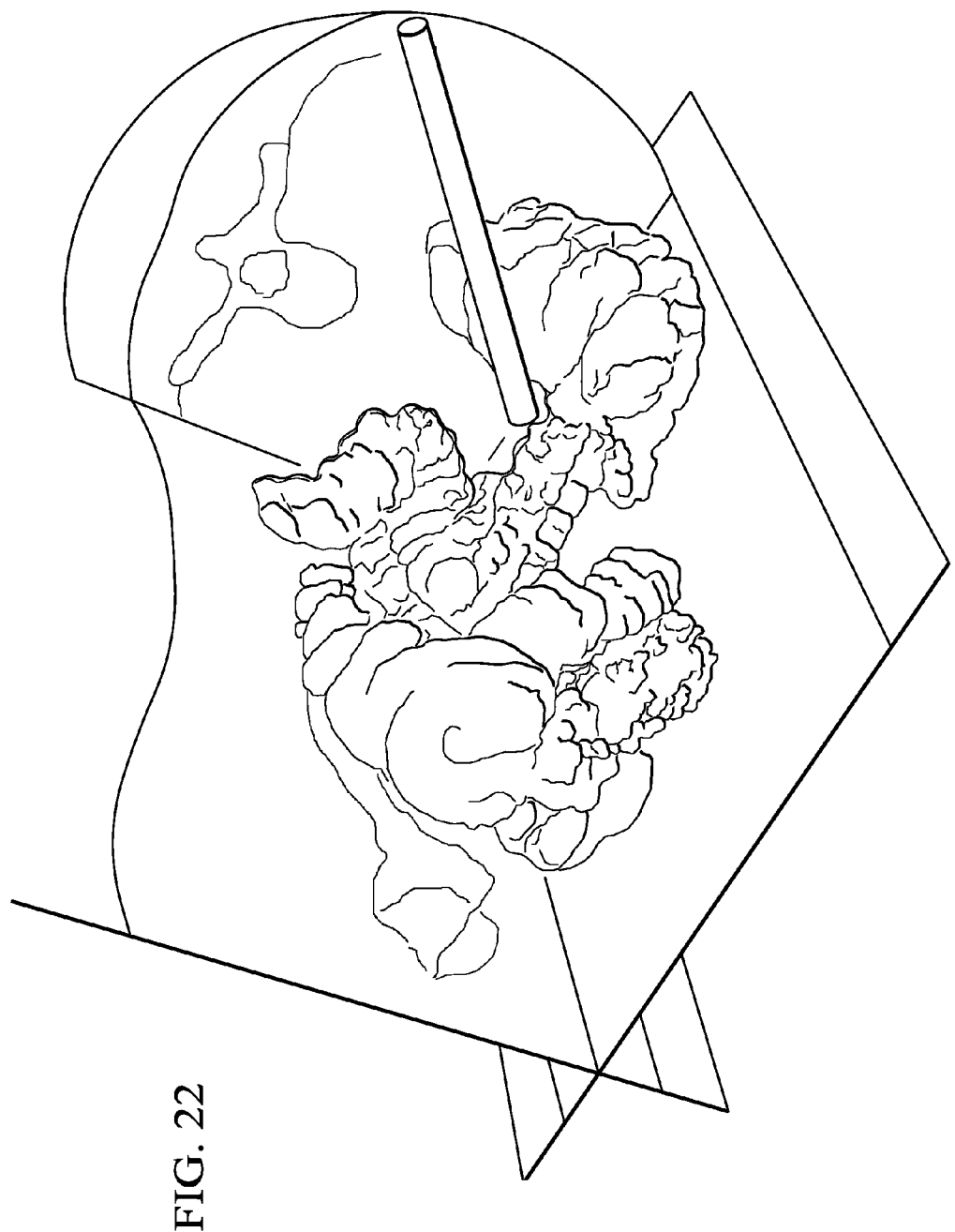
FIG. 22 shows an example of a display of slice images, which can be generated automatically by the VNS in response to movement of the endoscope.

An example of a display that can be generated using this technique is shown in FIG. 22, in which three orthogonal slice images (e.g., transverse, saggital and coronal planes) from intra-operative or pre-operative scan data are displayed coregistered with a 3D volumetric image of a portion of a colon. Also displayed is a computer-generated representation of the distal end of the scope, so that the user can see the relationship between the current viewpoint and the endoscopic camera viewpoint. Although the displayed images are selected based on the current position and orientation of the scope tip, the viewpoint of the displayed images can be a viewpoint other than the endoscopic camera viewpoint, as shown in FIG. 22.

Multi-Planar Reconstruction (MPR) can be used to facilitate this process. MPR is a well-known post-processing technique that can reconstruct axial scan images into coronal, sagittal and oblique anatomical planes. The same technique can also be used to obtain slices at any position and orientation through the volume. The data processing subsystem 44 can use the MPR algorithm to obtain the slices at the position and orientation of the tip of the scope and display them in real-time. The end result is that when the user moves the scope, the slices corresponding to that position and orientation are automatically displayed both over the 3D model and in the coronal, axial and sagittal windows.

II. Scope Tracking

As noted above, the VNS 30 uses signals from position/orientation sensors on the scope to track the current position and orientation of the distal tip of the scope. Techniques to accomplish this will now be described in greater detail.

Figure 10:
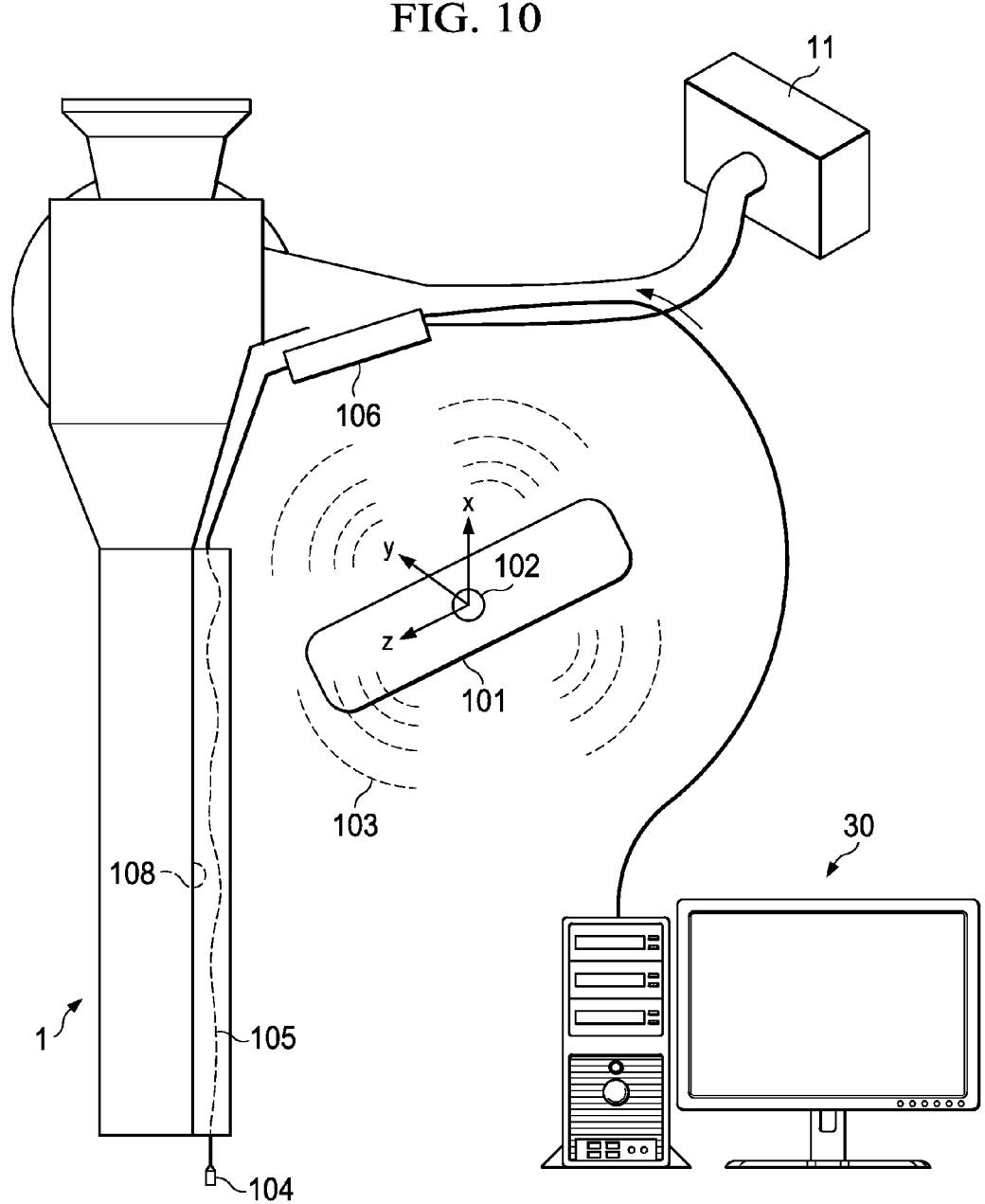
FIG. 10 schematically shows an example of a system configuration for tracking the position and orientation of the endoscope using electromagnetic sensors.

Referring that FIG. 10, in accordance with a first embodiment, an electromagnetic field generator is used as the center of the tracked volume and is hence placed under the patient table 101 at a configurable location. The location of the generator constitutes the origin 102 of the tracking system. In certain embodiments, each sensor 104 on the scope 1 contains three small wire coils (not shown) oriented perpendicular to each other. The electromagnetic field 103 generated by the generator induces current through these coils. The currents in these coils at any particular instant in time is dependent upon the electromagnetic field strength at the location of the sensor and the orientation of the sensor relative to the generator. Hence, the distance and orientation of the sensor 104 relative to the generator can be determined from those currents. Electromagnetic sensors such as the MicroBird sensors from Ascension Technology Corporation of Burlington, Vt., for example, are believed to be suitable for this purpose.

The currents produced by the coils in each sensor 104 are then transmitted by one or more thin wires 105 to a pre-amplifier 106 in the scope, which amplifies the current. The pre-amplified current is sent to a signal processor (not shown) within (or used by) the tracking subsystem 42 of the VNS 30, which computes the position and orientation of the sensor relative to the generator. The signal processor can be, for example, a conventional programmable microprocessor, digital signal processor, microcontroller, or other suitable processing device.

In certain embodiments of the invention, instead of using a separate channel for the sensor output wires 105, the light channel 108 of the scope 1, which is used to transmit light from the light source 11 to the scope tip, is used as a conduit for the sensor output wires 105, as depicted in FIG. 10. Since the dimension of the sensor output wires 105 is much smaller than the diameter of the light channel 108, embedding the wires 105 in the light channel 108 has negligible effect on the light transmitted and has the advantage of not requiring any protective coating over the transmitting wire 105, since the walls of the light channel serve that dual purpose.

Note that electromagnetic tracking of the scope may be susceptible to interference when operating in the vicinity of CRTs, MRI scanning devices or other devices that produce magnetic fields, as well as metal objects such as office furniture, that disrupt magnetic fields. Also, with electromagnetic tracking devices the working volume tends to be relatively small. Furthermore, electromagnetic tracking is expensive and sensitive to errors because of the complex signal processing involved.

Consequently, in alternative embodiments of the invention, optics are used to track the scope's distal tip rather than electromagnetic sensors. Optical tracking is advantageous, because it is benign, free from electromagnetic interferences, robust, and inexpensive. Optical trackers in general have high update rates, and sufficiently short delays. However, they are limited by line-of-sight problems, in that any obstacle between the sensor and the source can seriously degrade the tracker system's performance. To overcome this problem, a hybrid optical tracking approach can be used.

Figure 11:
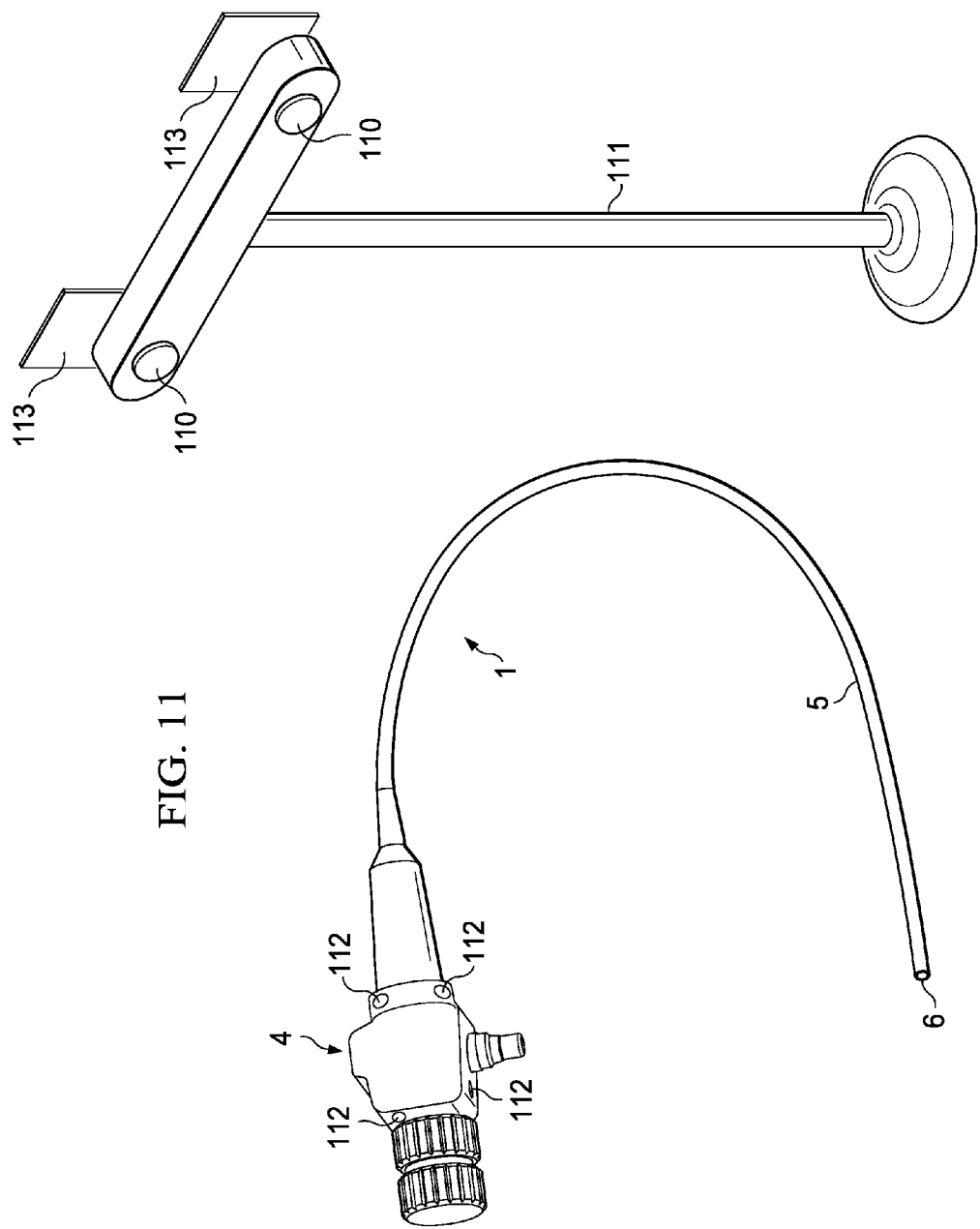
FIG. 11 schematically shows an example of a system configuration for tracking the position and orientation of the endoscope using optical curvature sensors.

In the hybrid approach, the base 4 of the flexible scope 1 can be tracked using conventional line-of-sight (e.g., LED based) optical trackers. In one embodiment, two cameras 110 are mounted on the ceiling or on a fixed frame 111, and several light emitting diodes (LEDs) 112 are placed at fixed, known positions on the base 4 of the scope, as shown in FIG. 11. Projections of the light emitted by the LEDs 112 onto the camera image planes 113 contain enough information to uniquely identify the position and orientation of the base 4 of the scope, using well-known methods. Various photogrammetric methods, particularly triangulation, can be used to compute this transformation and obtain the 3D coordinates of the base of the scope. These coordinates serve as a reference point for determining the position and orientation of the distal tip 6 of the scope 1.

For purposes of scope tracking, the LEDs 112 can be referred to in more general terms as location elements. As an alternative to LEDs 112, other types of location elements could be used, such as essentially any other type of device or devices by which the current position of the base 4 can be determined. Other types of location elements might include other types of light-emitting devices, one or more radio frequency (RF) transmitters, or even passive location markers such as reflective tags. In such alternative embodiments, the cameras 110 may be replaced by a different type of device, to be compatible with the type of location element(s) used, and may be an active device such as an RF transmitter if the location elements are passive. As another example, video cameras in combination with sophisticated shape recognition software can be used to identify and precisely determine the current position and orientation of the base 4 of the endoscope, without using any location elements on the base 4.

Figure 12:
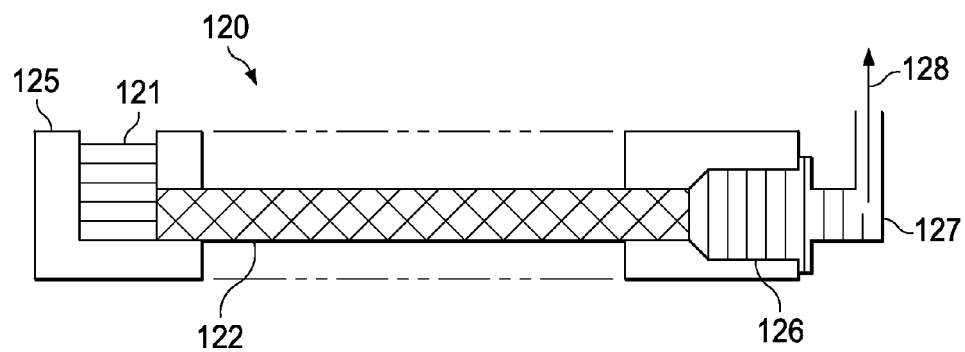
FIG. 12 shows the construction of an optical curvature sensor that can be used to track the endoscope.

The flexible portion 5 of the scope 1 can be tracked by using optical fiber curvature sensors. As represented schematically in FIG. 12, an optical fiber curvature sensor 120 includes a light source 121, optical fibers 122 to carry light from the light source 121, a connector 125 for the light source 121, a photodetector 126 to measure the intensity of light transmitting through the optical fibers 122, a connector 127 for the photodetector 126, an amplifier (not shown) to amplify the sensed signal and a signal processor (not shown). A typical phototransistor can be used as the photodetector 126. It is desirable that the selected type of photodetector be the type most sensitive to the wavelength of the light emitted from the light source 121. The output signal 128 from the optical curvature sensor can be transmitted back to the tracking subsystem of the VNS 30 via thin wires rounded through the light channel, as described above in relation to FIG. 10.

Figure 13:
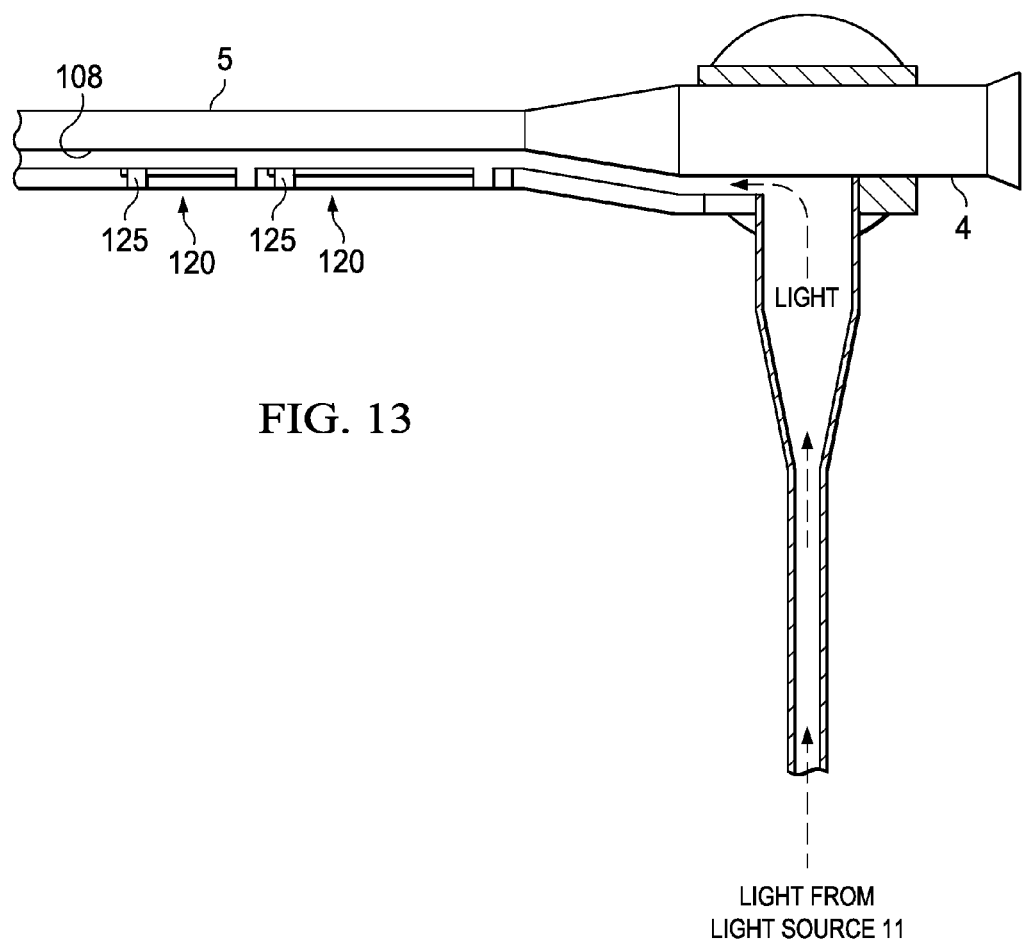
FIG. 13 shows the use of the light channel in the endoscope to provide a light source for optical curvature sensors on the endoscope.

Note that in certain embodiments of the invention, some of the abovementioned elements may be external to the optical curvature sensor 120; for example, the output signal amplifier and/or the signal processor can be in the tracking subsystem 42 of the VNS 30. As another example, the external light source 11 for the endoscope 1 can also serve as the light source 121 of all of the optical curvature sensors 120 in the endoscope 1. In that case, the light source connector 125 on each sensor 120 is connected with the light transmitting channel 108 (FIG. 10) of the endoscope 1, as shown in FIG. 13, to optically couple each sensor 120 to the light source 11.

Figure 14:
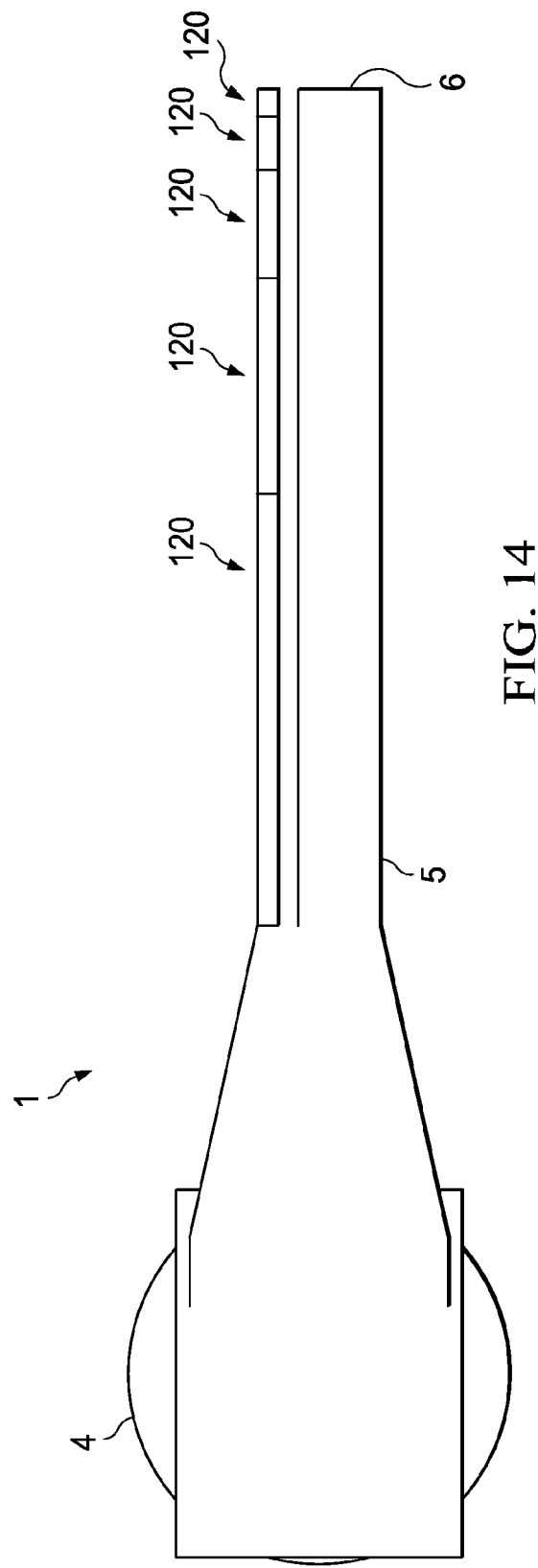
FIG. 14 shows the use of different length optical curvature sensors on the endoscope.

Since the output signal of the sensor corresponds to the average bend or twist in the sensor, depending on the type of the curvature sensor used, the length of the sensor is an important consideration. Hence, using a single sensor as long as the flexible portion 5 of the scope is not advisable, because the end-tip accuracy will be low. Instead, multiple fiber optic curvature sensors 120 can be placed in along the flexible portion 5 of the scope 1. As shown in FIG. 14, optical curvature sensors 120 of variable lengths can be placed along the flexible portion 5 of the scope 1, instead of using sensors of the same length. It is known a priori that the flexible portion 5 of the scope tends to deflect most at the distal tip 6 and least where it is closer to the base 5. With increasing proximity towards the distal tip 6, the possible deflection increases, and hence, the length of the curvature sensors 120 should decrease, as shown in FIG. 14.

Based on the data of the state of curvature at each sensor 120 and the known separation between sensors 120, the signal processing device in the VNS 30 can determine the shape, position and orientation of the flexible portion 5 of the scope 1. Those computed coordinates are with respect to a reference point, which in this case is the coordinates of the base 4, computed as described above. Therefore, if sufficient curvature measurements are taken and appropriately integrated, the exact position and orientation of the distal tip 6 of the scope can be computed, relative to the origin 102 of the tracking system (FIG. 10). This information can then be used to coregister live video from the endoscopic camera 9 with intraoperative and/or pre-operative scan images as described above.

Figure 15:
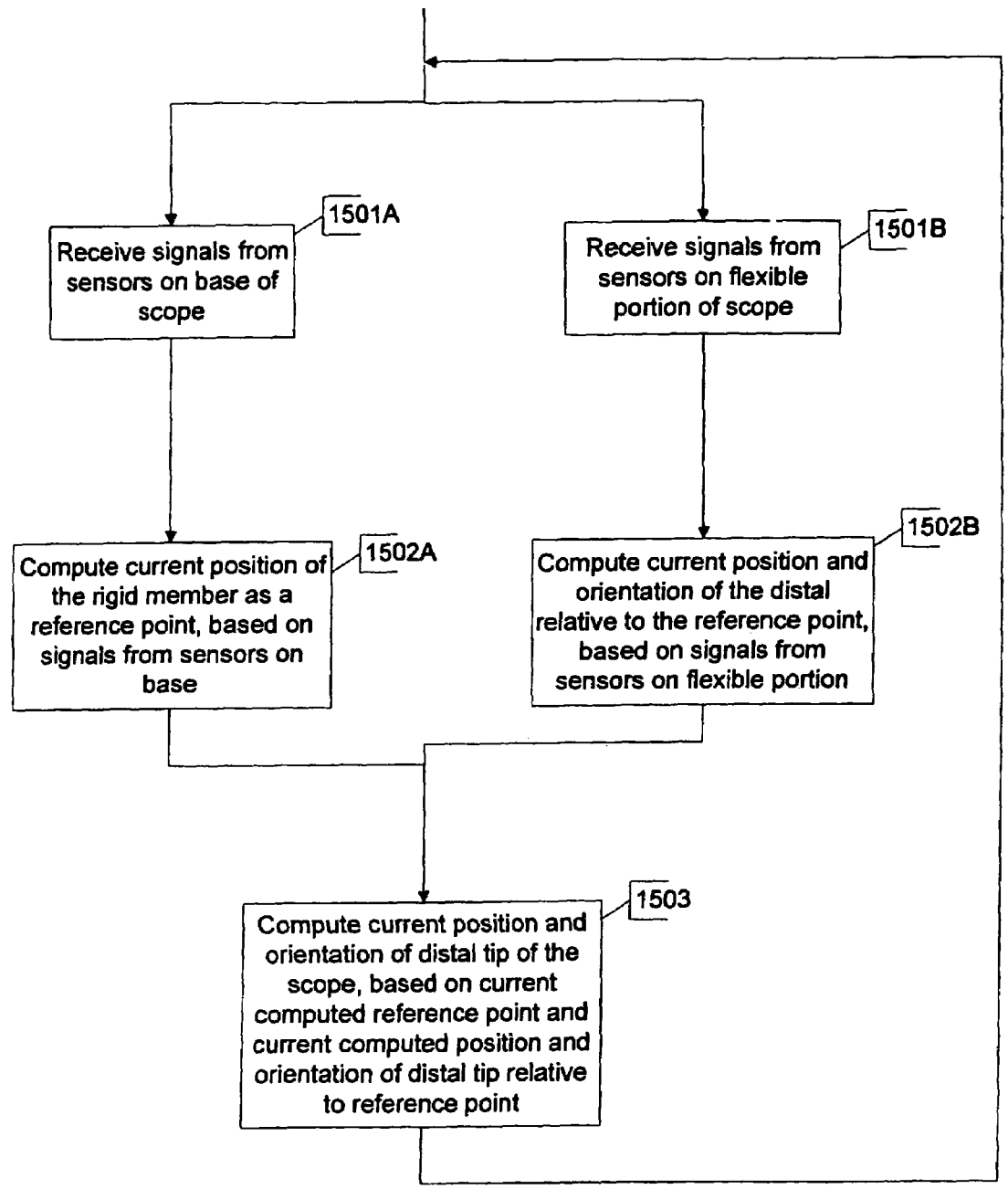
FIG. 15 illustrates an example of a process for determining the current position and orientation of the distal tip of the scope.

FIG. 15 illustrates an example of the process that may be performed by the tracking subsystem to determine the current position and orientation of the distal tip 6 of the scope 1, according to the hybrid approach discussed above. At 1501A, the VNS 30 receives signals from the position/orientation sensors or LEDs 112 on the base 4 of the scope 1. Concurrently with 1501A, at 1501B the tracking subsystem 42 receives signals from the position/orientation sensors 120 on the flexible portion 5 of the scope 1. At 1502A the tracking subsystem 42 then computes the current position of the base 4 of the scope 1 as a reference point (relative to the origin 102 of the tracking system), based on the signals from the sensors/LEDs 112 on the base, and concurrently at 1502B, it computes the current position and orientation of the distal tip 6 of the scope 1, relative to the reference point. At 1503, the tracking subsystem 42 computes the current position and orientation of the distal tip 6 of the scope 1 relative to the origin 102 of the tracking system, based on the current computed reference point and the current computed position and orientation of the distal tip 6 of the scope 1 relative to the reference point. The process then repeats using new inputs from the sensors.

III. Multi-Dimensional Navigation of Video

During endoscopic surgery, the video that is acquired from the endoscopic video camera 9 is a sequence of images captured through the scope 1, while the scope 1 is pointed in different directions at different instances in time. The video can be recorded as it is acquired. When playing back that video in the prior art, there is no known way to navigate through that video except to play it frame by frame, which provides only a single degree of freedom for visual navigation, i.e., time. Time is not always the best dimension in which to view the video, since it forces video playback from the scope's point of view.

It is therefore desirable to provide multi-dimensional navigation, i.e., visual navigation of endoscopic video with multiple degrees of freedom, or dimensions, i.e., not just time. The other navigation dimensions that the technique introduced here adds are position and orientation. More precisely, the technique which will now be introduced provides six degree of freedom for visual navigation of endoscopic video. In effect, this technique allows the user control of a virtual camera (point of view) that can be translated in three orthogonal axes in 3-D space as well as allowing control of vertical panning (pitch), horizontal panning (yaw) and tilt (roll) of the virtual camera, as well as zoom.

Figure 16:
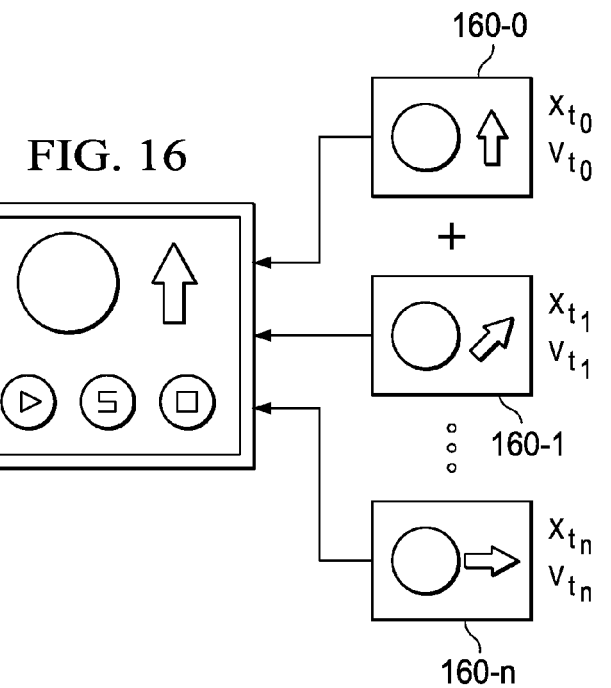
FIG. 16 shows the tagging of video frames with position and orientation information.

This technique will be described now is reference to FIGS. 16 through 19. Initially, the position x(t) and orientation v(t) of each captured video frame 160-$i$ or image is determined when the frame is captured, and the frame is tagged with this information, as shown in FIG. 16. Hence, the acquired video becomes a set of images with known positions and orientations.

Figure 17:
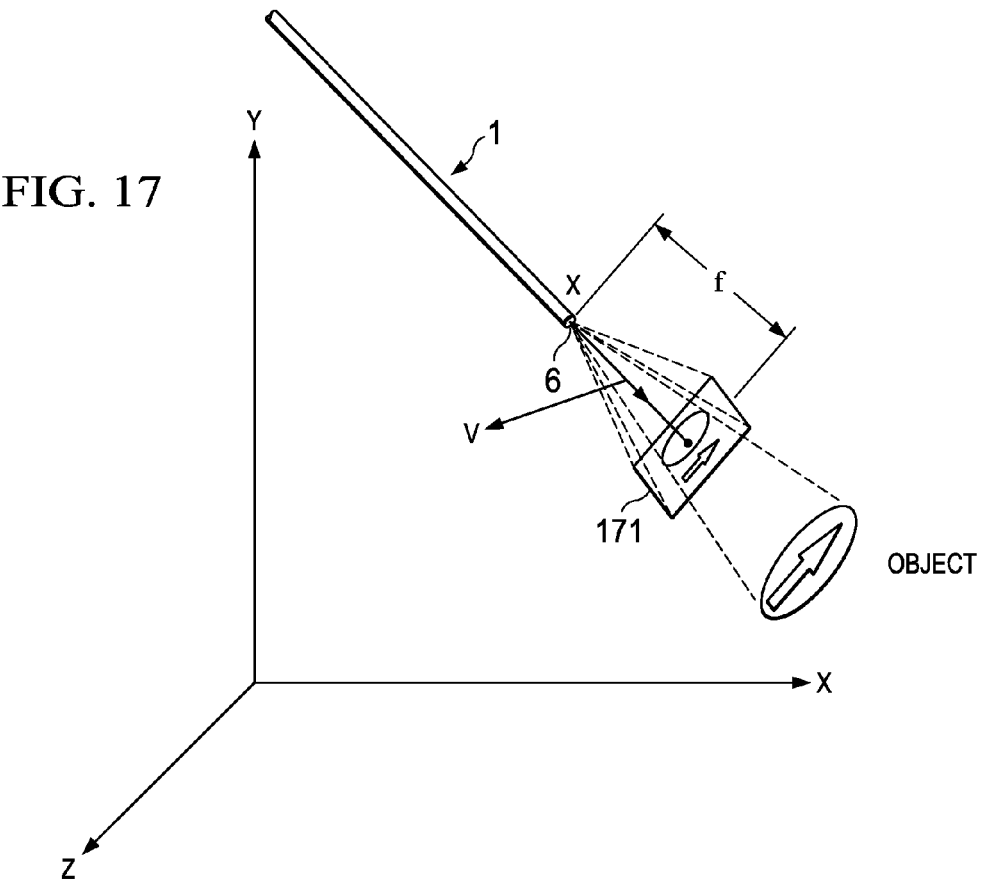
FIG. 17 illustrates the relationship between the endoscope tip, the image plane and the object being viewed.

Referring to FIG. 17, given the position X and unit orientation vector V of the scope's distal tip 6, the position X' and unit orientation vector V' of the image plane 171 can be computed as X'=X+f.V' where X=[x,y,z]T, and V=[i,j,k] T and f is the distance between the distal tip 6 and the image plane 171.

V'=V since the normal to the image plane 171 is the orientation vector of the distal tip 6.

X' and V' can then be used to place the image plane 171 in virtual 3D space at the position X' and the orientation V'. The OpenGL and VTK software libraries can be used to place the image at the specified position and orientation in space.

Figure 18:
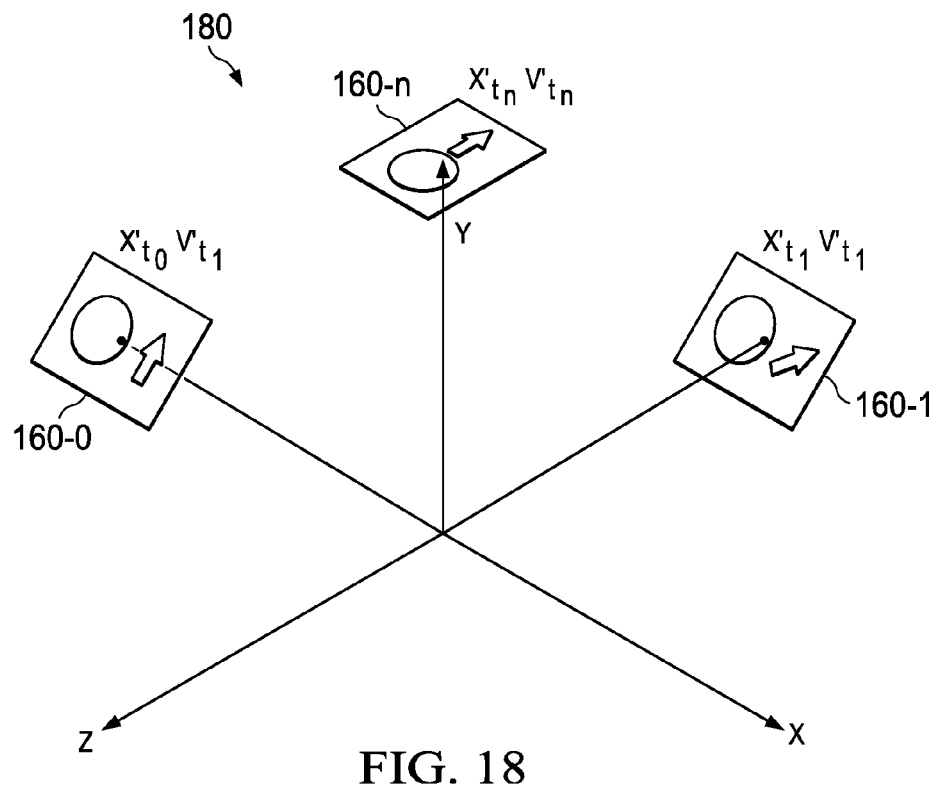
FIG. 18 illustrates the placement of various video frames into a common 3D coordinate space.

Hence, as the scope tip's position and orientation information is obtained, a frame or image 160-$i$ is grabbed from the video feed and placed in the 3D window coordinate system 180, as illustrated in FIG. 18. Also text indicating the timestamp can be overlaid on each frame 160-$i$, so that the user will know at what instant the frame was grabbed.

Thus, at any given point in the surgery, when the user wishes to navigate through the grabbed frames, he navigates through the 3D space by using a mouse, keyboard, or other user input device. The class vtkRenderWindowInteractor in the VTK library captures mouse and keyboard events in a render window. Accordingly, mouse and keyboard events can be applied to control the viewpoint and the orientation of the virtual camera associated with the render window in which the frames or images are being placed. This in effect allow the user to navigate through the video with six degrees of freedom, i.e., translation along all three coordinate axes as well as pitch, yaw and roll, of the virtual camera. In order to provide smooth transitions between intersecting image planes, interpolation can also be employed. For example, bilinear interpolation, nearest neighbors interpolation or other types of interpolation can be used.

Figures 19A, 19B:
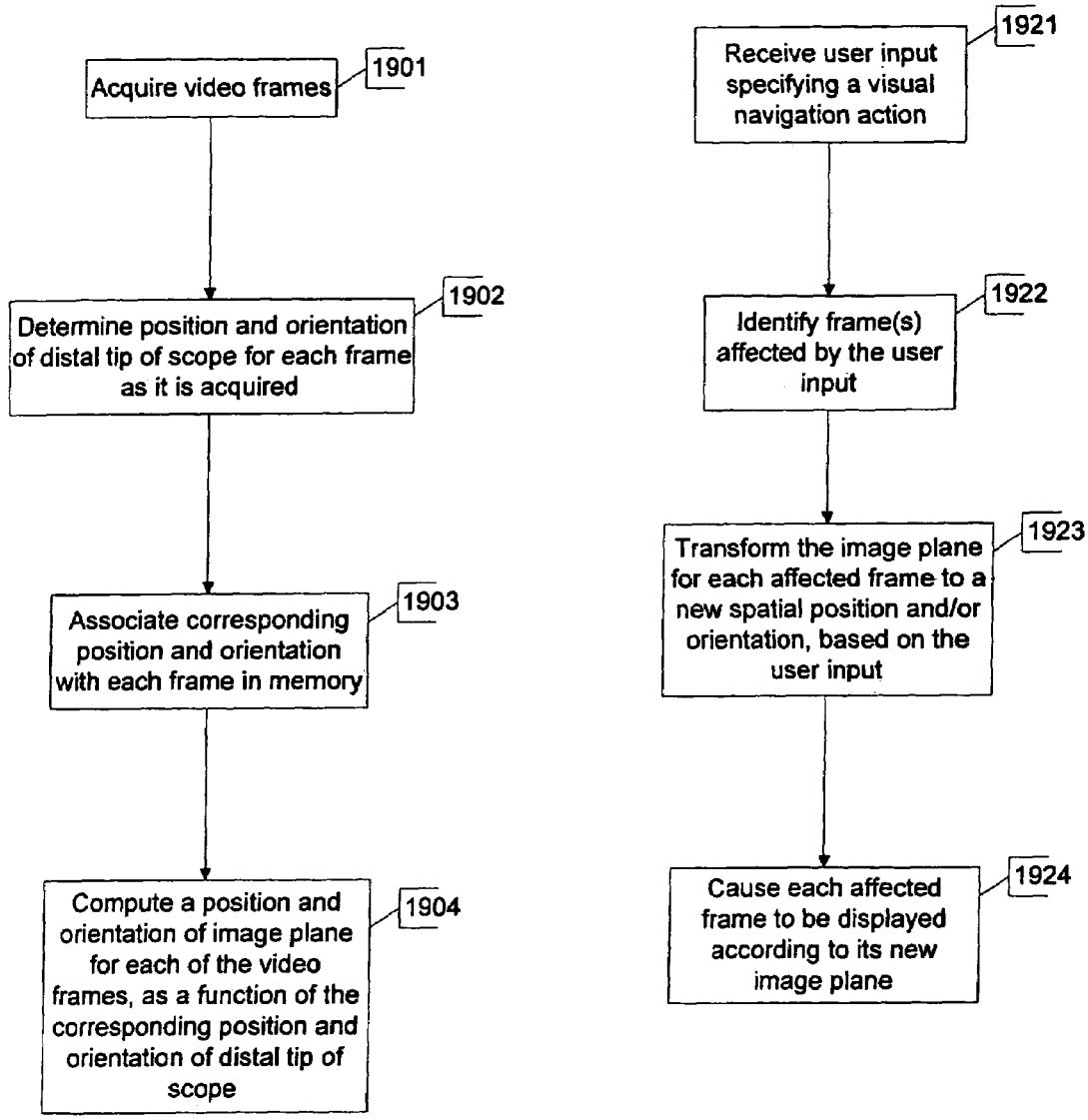
FIG. 19A shows a process of acquiring and processing video data to enable subsequent visual navigation.
FIG. 19B shows a process by which a user can visually navigate through video that has been processed as in FIG. 19A.

FIGS. 19A and 19B show processes associated with this navigation technique. These processes are performed by the multi-dimensional video generation module 78 (FIG. 6). More specifically, FIG. 19A shows a process of acquiring and processing video data in order to enable subsequent visual navigation as described above. At 1901 the VNS 30 acquires video frames from the endoscopic camera video feed. At 1902 the VNS 30 determines the position and orientation of the distal tip of the scope for each frame as it is acquired. At 1903 the VNS 30 associates the corresponding position and orientation information with each frame in memory. An at 1904 the VNS 30 computes, in the manner described above, the position and orientation of the image plane for each of the video frames, as a function of the corresponding position and orientation of the distal tip for each frame.

FIG. 19B shows the process by which the user can visually navigate through video that has been processed as described above. Using this process, a user can navigate previously-recorded processed video, or a user can navigate video as it is being acquired, in near real-time (subject only to the delay required to process the video as described in reference to FIG. 19A). At 1921 the VNS 30 receives user input specifying a visual navigation action. The action may be, for example, a mouse input or joystick input specifying movement of the virtual camera in translation and/or in rotation relative to any one or more of the three coordinate axes. In 1922 the VNS 30 identifies the frame or frames that are affected by the user input. The VNS 30 then transforms the image plane for each affected frame to a new spatial position and orientation, based on the user input, as described above. The VNS 30 then causes each affected frame to be displayed according to its new image plane at 1924.

IV. Model Fitting Measurement Technique

It is desirable to be able to obtain in vivo measurements of anatomical features in the body during an endoscopic procedure. For example, during endoscopic surgery it may be desirable to know the size of a colon polyp, such as polyp 201 shown in FIG. 20. If an incision needs to be made, it is desirable to know the required size of the incision so that the instrument used for making the incision can be selected or configured accordingly. Alternatively, if there is a need to ablate tissue, then it is desirable to know the size of the region that needs to be ablated, so that the ablation instrument strength and range can be configured. If an implant needs to be placed inside the body, such as in the esophagus for the GERD procedure or a heart valve implant needs to be positioned, it is desirable to know the size of the opening so that the implant's size, orientation and position can be selected.

With this in mind, the VNS 30 can also include capability to obtain approximate measurements of an anatomical feature or region of interest in vivo, through the measurement subsystem 43. The approach introduced here includes fitting a user selected implicit model to a set of points that reside on the surface of the anatomical region of interest. Implicit functions are of the form $F(x,y,z)$=constant.

An example of an implicit function that can be used is a sphere S of radius R and centered at the origin, which can be described by the equation $F(x,y,z) = R^2 - x^2 - y^2 - z^2$. The equation $F(x, y, z) < 0$ describes a sphere that lies inside the sphere S, and when $F(x,y,z) > 0$, a sphere that lies outside the sphere S is defined. The unknown in the above implicit function is the radius R of the sphere. Note that the technique described here is not restricted to one implicit function; a list of implicit functions may be made available, from which the user can choose.

Figure 20:
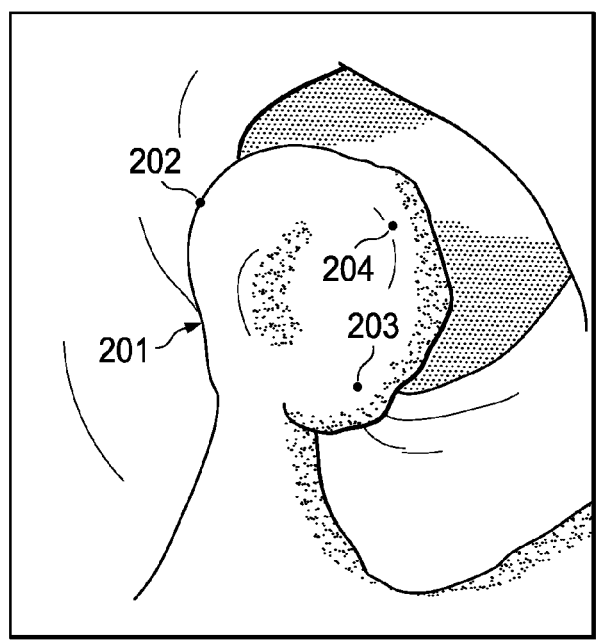
FIG. 20 illustrates an endoscopic camera view of an anatomical object.

The set of points needed to fit the implicit function are initially collected by the user's pressing a predetermined control input (e.g., pressing a designated button on the scope 1 or the endoscopic video camera 9) when the tracked distal tip 6 of the scope is touched to three or more locations of the surface of the anatomical feature of interest, such as locations 202, 203 and 204 on the surface of the polyp 201 shown in FIG. 20. FIG. 20 illustrates an endoscopic camera view of a polyp.

The implicit model fitting problem can be phrased as follows:

The goal is to approximate a real valued function $f(x)$ by $s(x)$ given the set of values $f=\{f1, \ldots, fN\}$ at the distinct points $X=\{x_1, \ldots, x_N\} \subset \mathbb{R}^d$.

For the fitting process a least squares schema can be used, that minimizes the distance between the global implicit surface field function and the 3-D points. Orthogonal distance regression can be used to minimize the distance function, where the sum of squares of orthogonal distances from the data points to the surface is minimized. An alternative approach can use radial basis functions to approximate the implicit surface. Note that a product FastRBF from ARANZ can be used to smoothly interpolate scattered 2D and 3D data with Radial Basis Functions (RBFs).

Once the model is fitted, it is meshed and displayed to the user along with the associated parameters. The user can mark additional points on the surface to improve the accuracy of the model; in that sense, the model and this approach in general are adaptive.

The user can also perform binary operations of union and intersection between models. One possible use of such an operation is to allow the surgeon to see how the model of an anatomical feature intersects with a graphical model of a surgical implant. Measurements from the anatomical model will be the attributes associated with the selected implicit function, such as volume, surface area, minimum extent, maximum extent, etc.

Figure 21:
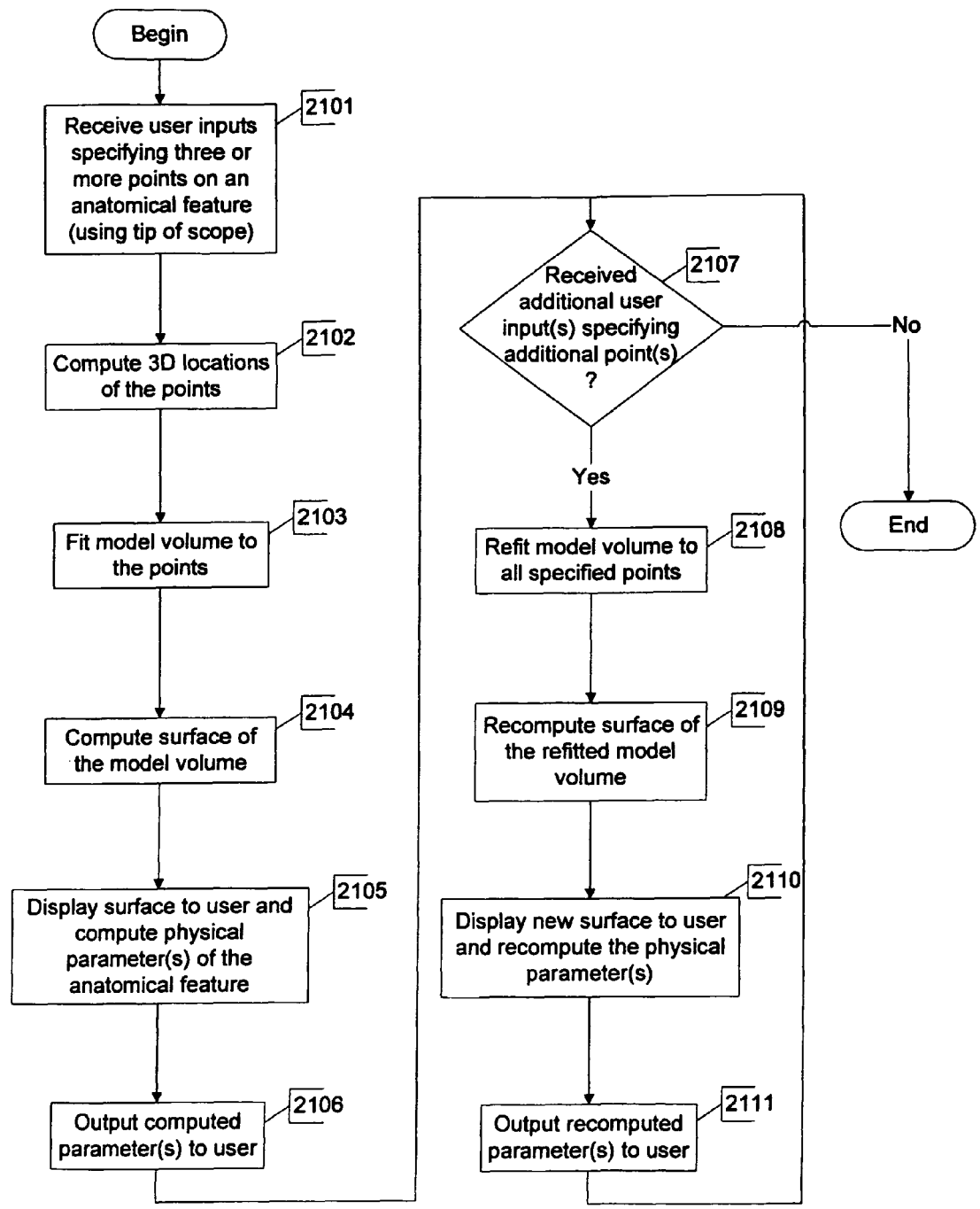
FIG. 21 shows a process of automatically measuring one or more parameters of an anatomical feature.

FIG. 21 illustrates an example of this process. At 2101 the VNS 30 receives user input specifying three or more points on the surface of an anatomical feature. As noted above, this can be done by the user's touching the distal tip 6 of the scope 1 to the surface of the anatomical feature and providing a predetermined control input at each point to command the system to capture the coordinates of the point. At 2102 the tracking subsystem 42 computes the 3D locations of the captured points. The measurement subsystem 43 then fits a model volume (e.g., a sphere), as defined by the user-selected implicit function, to the captured points. At 2104 the measurement subsystem computes a mesh to form the surface of the model volume. At 2105 the VNS 30 causes the surface to be displayed to the user, and the measurement subsystem 43 computes one or more physical parameters of the anatomical feature as represented by the model surface, such as its volume. The parameters that can be computed depend on the implicit model that is used. If the implicit model is a sphere, then another parameter that can be computed to reflect an attribute of the anatomical feature is the surface area, for which a standard formula can be used. Other parameters can also be calculated using standard formulas, depending on the implicit model.

The computed parameter or parameters are then output to the user at 2106 by the user interface subsystem 46. The user can at this point specify one or more additional points on the surface of the anatomical feature to refine the model and, hence, the measurements. If no such additional user inputs are received (2107), the process ends.

If additional user inputs specifying points are received, the model is then refit to all of the specified points at 2108, and the surface of the refitted model is then computed at 2109. The new surface is displayed to the user and the parameter or parameters are recomputed at 2110. The recomputed parameter or parameters are then output to the user at 2111.

V. Path Computations and Display

Figure 23:
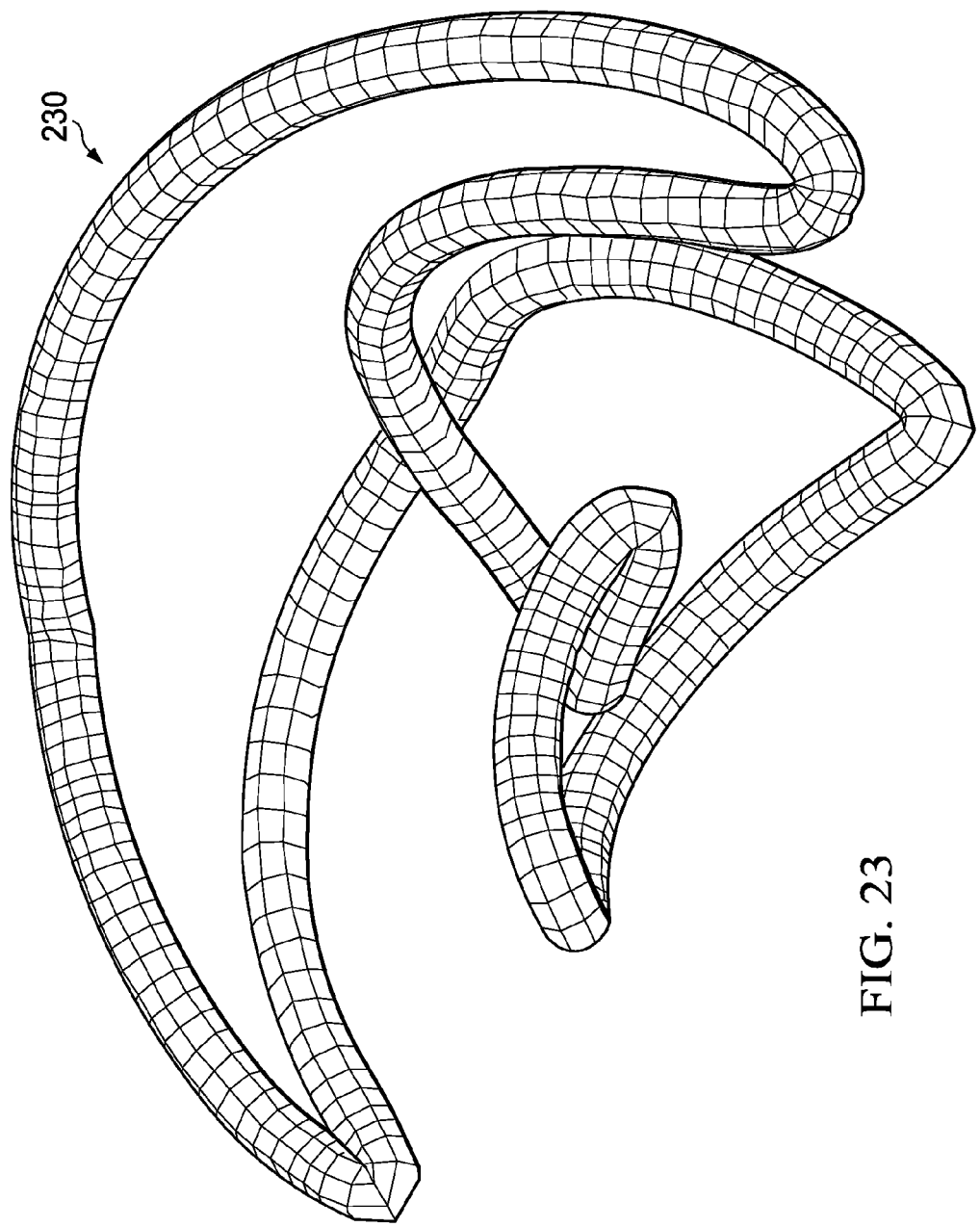
FIG. 23 shows an example of a 3D rendering of a computed path taken by an endoscope during endoscopic surgery.

As noted above, the data processing subsystem 44 in certain embodiments includes a path correlation module 79 (FIG. 6) that can compute the path taken by the scope (or any other surgical instrument) during a procedure and various attributes and parameters related to that path. The path correlation module 79 receives data indicating the current position and orientation of the scope from the tracking subsystem 42. It converts the data into a dataset representing the path taken by the scope, and transforms that dataset into graphic model parameters to enable the path to be rendered and displayed to a user in 3D. An example of how such a path can be displayed to a user by the VNS 30 is shown in FIG. 23. The path, such as path 230 in FIG. 23, may be shown in 3D and in color, where different colors are used to indicate the distance between particular points on the path 230 and the viewing plane.

Figure 24:
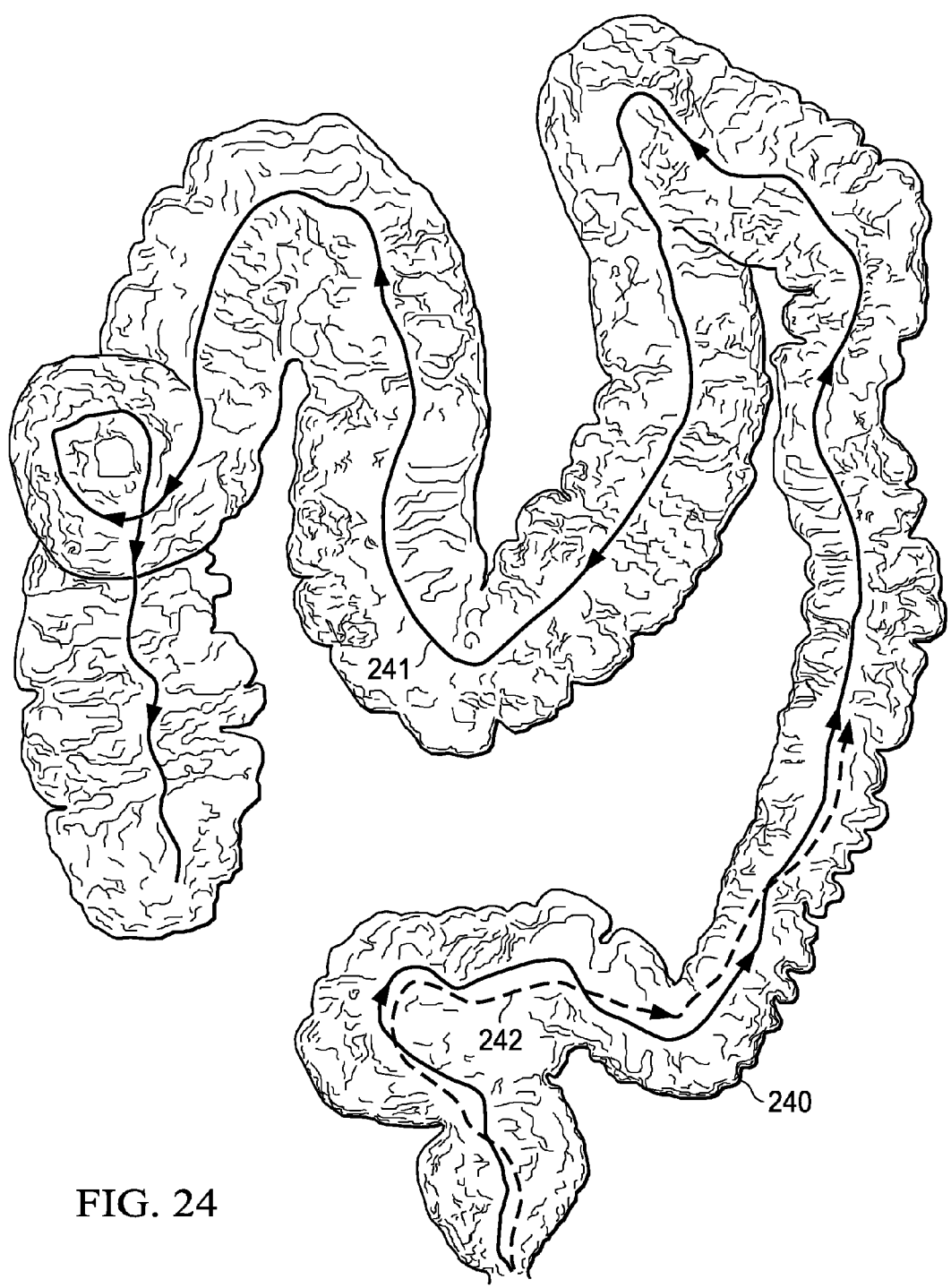
FIG. 24 shows an example of how the spatial relationship between two paths can be displayed.

The path correlation module 79 can also determine a correlation between two or more paths, e.g., between the actual path of the scope (or other medical instrument) and a predefined reference path, and can display the two paths and output an indication of that correlation to a user. FIG. 24 shows an example of how the spatial relationship between two paths can be displayed. More specifically, FIG. 24 shows an example of a display that includes a 3D rendering of a colon 240, a pre-surgery planned path 241 for the endoscope, and the actual path 242 taken by the endoscope (which may be determined in real-time or based on previously recorded movements of the scope). With such a display, the user can easily see the deviation of the actual path 242 from the planned path 241.

Figure 27:
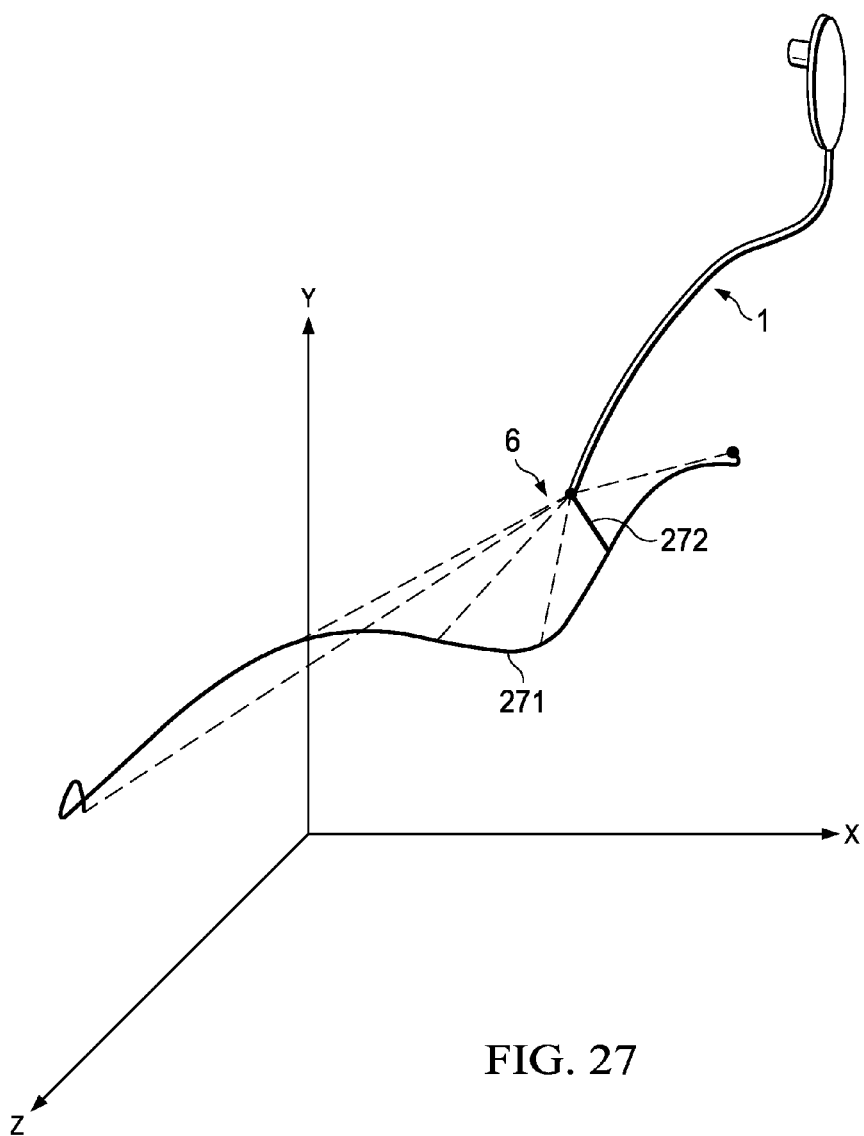
FIG. 27 illustrates the computation of correlation between the current position of the endoscope tip and a reference path.

The correlation may be determined as the amount and location of deviation between a given position and orientation of the scope from the reference path. More specifically, this may be determined by first finding a position along the reference path which is closest to a current position of the scope, and then determining the deviation as the distance between the current location of the scope and that position along the reference path. FIG. 27 illustrates the computation of correlation between the current position of the scope tip 6 and a reference path 271, where the correlation is represented by line 272.

The path correlation module 79 can also determine a correlation between two recorded paths (e.g., an amount and location of deviation between the two paths) and output an indication of that correlation to a user. An example of a process for determining a correlation between two recorded paths is illustrated in FIG. 28.

Figure 25:
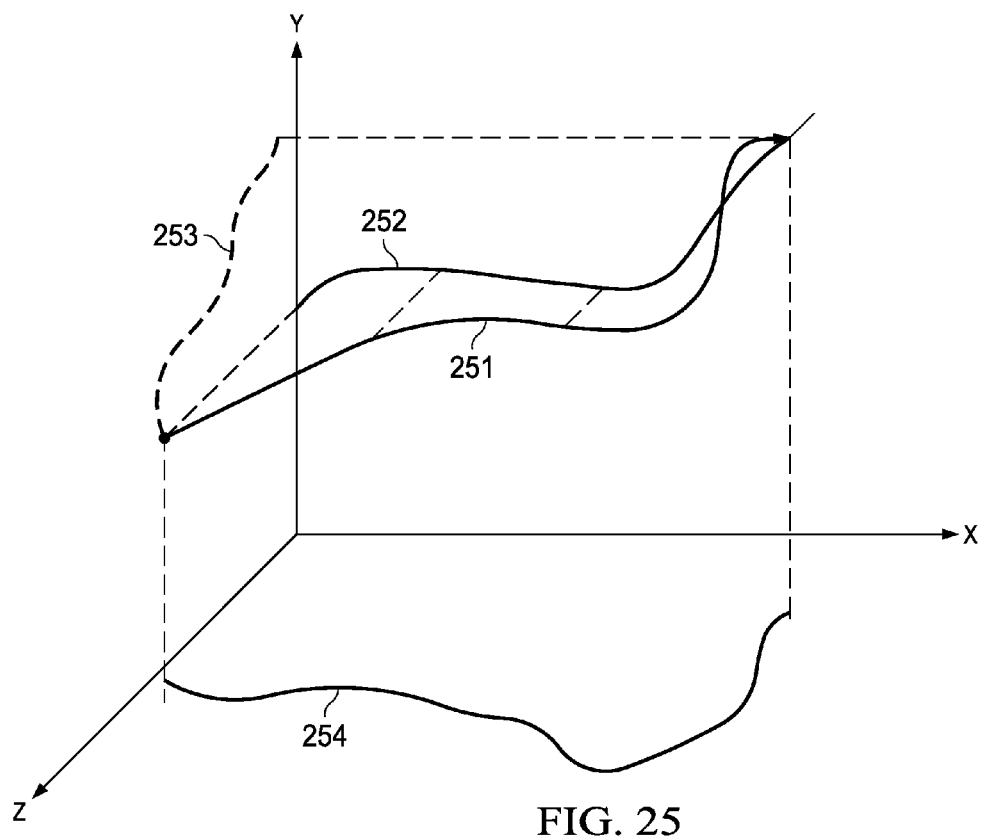
FIG. 25 illustrates an example of projecting a path onto three orthogonal planes.
Figure 28:
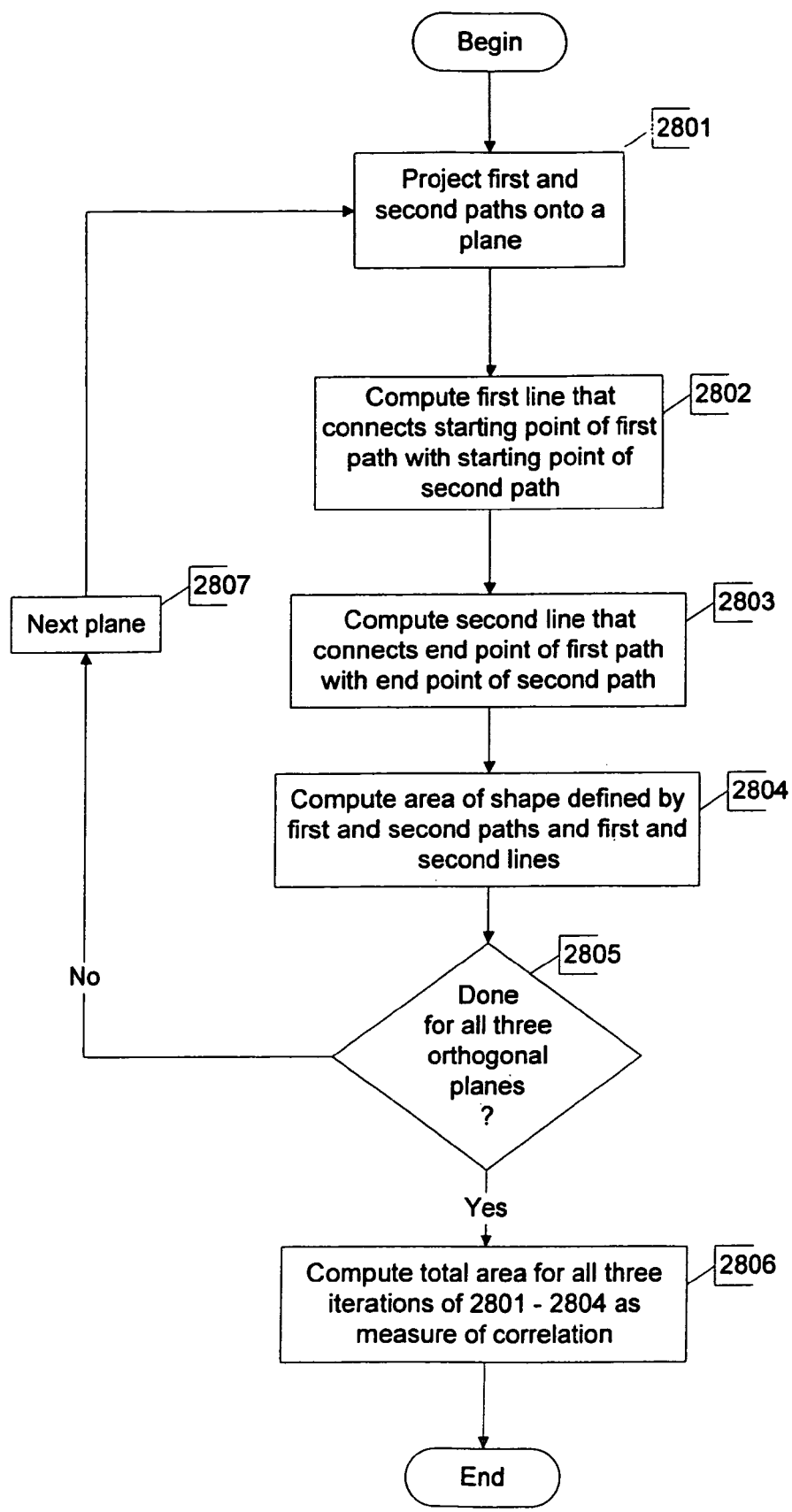
FIG. 28 shows an example of a process for determining a correlation between two paths.

Referring to FIG. 28, at 2801 the process projects both a first recorded path and a second recorded path onto one of the three orthogonal image planes, i.e., x-y, y-z or z-x plane (this operation will also be done for the other two planes, as described below). FIG. 25 illustrates an example of projecting a path onto three orthogonal planes. Projection 252 is the projection of path 251 onto the x-y plane, projection 253 is the projection of path 251 onto the y-z plane, and projection 254 is the projection of path 251 onto the z-x plane.

Figure 26:
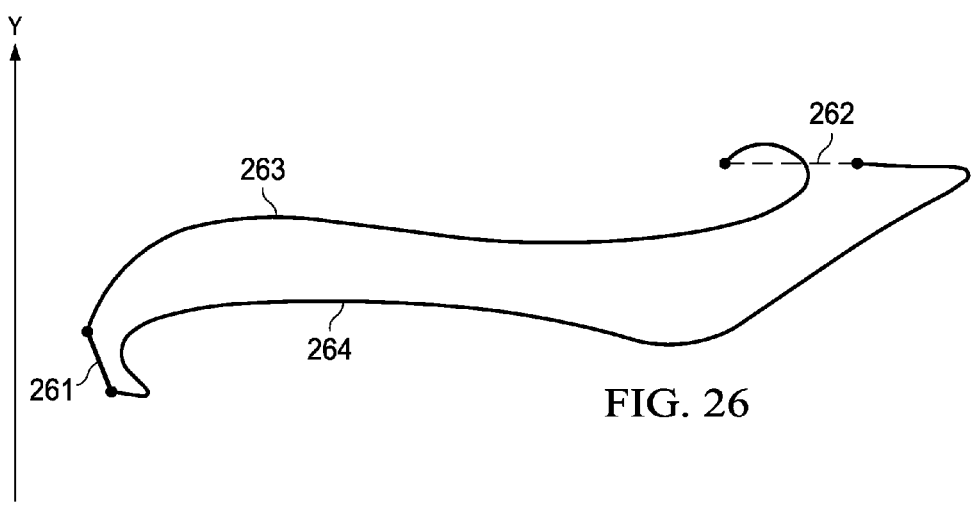
FIG. 26 illustrates the connection of endpoints of two paths.

At 2802 the process computes a first line that connects the starting point of the first recorded path with the starting point of the second recorded path and, at 2803, computes a second line that connects the end point of the first recorded path with the end point of the second recorded path. Operations 2802 and 2803 are illustrated in FIG. 26, in which lines 261 and 262 connect the starting point and endpoints, respectively, of two recorded paths 263 and 264 projected onto a plane.

At 2804 the process computes an area, medial axis, of a shape, the boundary of which is collectively defined by the first and second recorded paths and the first and second lines. Operations 2801 through 2804 are then repeated for the y-z and the z-x planes (2805/2807). At 2806 the process computes the total area for all three iterations of 2801 through 2804 as a measure of the correlation between the first and second recorded paths.

The path correlation module 79 can also identify a landmark along the path (e.g., from previously recorded user input, such as a voice input or a button click on the endoscopic video camera, identifying the landmark) and metadata associated with the landmark (e.g., voice and/or text), and transform an associated position and orientation of the endoscope and the metadata into graphics primitives, to allow rendering and display of data indicative of the associated position, orientation and the metadata. In addition, the path correlation module 79 can also compute the distance between the current position of the endoscope and the landmark and cause an indication of the distance to be output to a user.

Thus, a visual navigation system for use in endoscopic surgery, particularly endoluminal surgery, has been described. The techniques introduced above, including all of the modules of the VNS 30, can be implemented in logic such as special-purpose hardwired circuitry, software and/or firmware that runs on one or more programmable processors, or in a combination thereof. Special-purpose hardwired circuitry may be in the form of, for example, one or more application-specific integrated circuits (ASICs), programmable logic devices (PLDs), field-programmable gate arrays (FPGAs), etc.

Software or firmware to implement the techniques introduced above may be stored on a machine-readable medium and may be executed by one or more general-purpose or special-purpose programmable microprocessors. A "machine-accessible medium", as the term is used herein, includes any mechanism that provides (i.e., stores and/or transmits) information in a form accessible by a machine (e.g., a computer, network device, personal digital assistant (PDA), manufacturing tool, any device with a set of one or more processors, etc.). For example, a machine-accessible medium includes recordable/non-recordable media (e.g., read-only memory (ROM); random access memory (RAM); magnetic disk storage media; optical storage media; flash memory devices; etc.), etc.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A computer-implemented method comprising:
    acquiring, by the computer, video frames of an anatomical region of interest from a video camera optically coupled to an endoscope during an endoscopic procedure, the video frames being acquired in a sequence of instances of time;
    determining, by the computer, a position and orientation of a distal tip of the endoscope for each of the video frames as the video frames are acquired;
    associating, by the computer, each of the video frames with data indicative of the position and orientation of the distal tip as the video frames were acquired; and
    processing, by the computer, the video frames to produce a plurality of processed frames, to enable a user to visually navigate the video frames of the anatomical region of interest during the endoscopic procedure out of sequence using the position and orientation data associated with the processed frames, and with at least one degree of freedom that is not represented in the sequence of instances of time of the video frames acquired from the camera.

2. A method as recited in claim 1, wherein said processing the video frames comprises:
    processing the video frames to enable the user to visually navigate the anatomical region of interest with six degrees of freedom.

3. A method as recited in claim 1, wherein said processing the video frames comprises:
    processing the video frames to enable the user to visually navigate the anatomical region of interest with control of a virtual endoscope point of view using spatial translation in each of three dimensions and yaw, pitch and roll.

4. A method as recited in claim 1,
    wherein said processing the video frames comprises:
        computing a position and orientation of an image plane for each of the video frames as a function of the corresponding position and orientation of the distal tip of the endoscope; and
        transforming the image planes for the frames to user-specified spatial positions and orientations, in response to user inputs.

5. A method as recited in claim 4, further comprising:
    applying interpolation to smooth transitions between intersecting image planes.

6. A computer-implemented method comprising:
    acquiring, by the computer, video frames of an anatomical region of interest from a video camera optically coupled to a flexible endoscope during an endoscopic procedure, the video frames being acquired in a sequence of instances of time;

determining, by the computer, a position and orientation of a distal tip of the flexible endoscope for each of the video frames as the video frames are acquired;

associating, by the computer, in memory, with each of the video frames, data indicative of the position and orientation of the distal tip as the video frames were acquired; and processing, by the computer, the video frames to produce a plurality of processed frames, to enable a user to visually navigate the video frames of the anatomical region of interest during the endoscopic procedure out of sequence using the position and orientation data associated with the processed frames by controlling a virtual endoscope point of view with spatial translation in each of three dimensions and yaw, pitch and roll.

7. A method as recited in claim 6, wherein said processing comprises:

computing a position and orientation of an image plane for each of the video frames as a function of the corresponding position and orientation of the distal tip of the endoscope; and in response to user input specifying a visual navigation action, transforming the image plane of one of the frames to a new spatial position or orientation based on the user input.

8. A method as recited in claim 7, further comprising:
causing said one of the frames to be displayed according to said transformed image plane.

9. A method as recited in claim 6, further comprising:
using interpolation to smooth transitions between intersecting image planes.

10. A system comprising:
a processor; and
a memory coupled with the processor and storing instructions which, when executed by the processor, cause the processor to
  acquire video frames of an anatomical region of interest from a video camera that is optically coupled to an endoscope during an endoscopic procedure, the video frames being acquired in a sequence of instances of time;
  determine a position and orientation of a distal tip of the endoscope for each of the video frames as the video frames are acquired;
  associate each of the video frames with data indicative of the position and orientation of the distal tip as the video frames were acquired; and
  process the video frames to produce a plurality of processed frames, to enable a user to visually navigate the video frames of the anatomical region of interest during the endoscopic procedure out of sequence using the position and orientation data associated with the processed frames, and with at least one degree of freedom that is not represented in the sequence of instances of time of the video frames acquired from the camera.

11. A system as recited in claim 10, further comprising a user interface subsystem to receive user inputs for controlling visual navigation of the anatomical region of interest.

12. A system as recited in claim 10, wherein the video processing subsystem comprises:
logic to process the video frame data to produce the plurality of frames, to enable the user to visually navigate the anatomical region of interest with six degrees of freedom.

13. A system as recited in claim 10, wherein the video processing subsystem comprises:
logic to process the video frames to enable the user to visually navigate the anatomical region of interest with control of a virtual endoscope point of view using spatial translation in each of three dimensions and yaw, pitch and roll.

14. A system as recited in claim 13,
wherein the video processing subsystem comprises:
logic to compute a position and orientation of an image plane for each of the video frames as a function of the corresponding position and orientation of the distal tip of the endoscope; and
logic to transform the image planes for the frames to user-specified spatial positions and orientations, in response to user inputs.

15. A system as recited in claim 14, further comprising logic to apply interpolation to smooth transitions between intersecting image planes.

16. A non-transitory machine-readable storage medium storing instructions that, when executed, cause a processing system to perform a method comprising:
acquiring video frames of an anatomical region of interest from a video camera optically coupled to an endoscope during an endoscopic procedure, the video frames being acquired in a sequence of instances of time;
determining a position and orientation of a distal tip of the endoscope for each of the video frames as the video frames are acquired;
associating each of the video frames with data indicative of the position and orientation of the distal tip as the video frames were acquired; and
processing the video frames to produce a plurality of processed frames, to enable a user to visually navigate the video frames of the anatomical region of interest during the endoscopic procedure out of sequence using the position and orientation data associated with the processed frames, and with at least one degree of freedom that is not represented in the sequence of instances of time of the video frames acquired from the camera.

17. The non-transitory machine-readable storage medium as recited in claim 16, wherein said processing the video frames comprises:
computing a position and orientation of an image plane for each of the video frames as a function of the corresponding position and orientation of the distal tip of the endoscope; and
transforming the image planes for the frames to user-specified spatial positions and orientations, in response to user inputs.

* * * * *